US012350523B2

(12) United States Patent
Dempsey et al.

(10) Patent No.: US 12,350,523 B2
(45) Date of Patent: Jul. 8, 2025

(54) MRI GUIDED RADIOTHERAPY

(71) Applicant: ViewRay Systems, Inc., Denver, CO (US)

(72) Inventors: James F. Dempsey, Pebble Beach, CA (US); Iwan Kawrykow, Sofia (BG)

(73) Assignee: ViewRay Systems, Inc., Denver, CO (US)

( * ) Notice: Subject to any disclaimer, the term of this patent is extended or adjusted under 35 U.S.C. 154(b) by 133 days.

(21) Appl. No.: 17/969,544

(22) Filed: Oct. 19, 2022

(65) Prior Publication Data

US 2023/0125842 A1   Apr. 27, 2023

Related U.S. Application Data

(60) Provisional application No. 63/270,862, filed on Oct. 22, 2021.

(51) Int. Cl.
| | | |
|---|---|---|
| *A61N 5/10* | (2006.01) | |
| *A61B 5/055* | (2006.01) | |
| *G01R 33/385* | (2006.01) | |
| *G01R 33/50* | (2006.01) | |

(52) U.S. Cl.
CPC ............ *A61N 5/1068* (2013.01); *A61B 5/055* (2013.01); *A61N 5/1049* (2013.01); *A61N 5/1071* (2013.01); *G01R 33/385* (2013.01); *G01R 33/50* (2013.01); *A61N 2005/1055* (2013.01); *A61N 2005/1074* (2013.01)

(58) Field of Classification Search
CPC .. A61N 5/1068; A61N 5/1049; A61N 5/1071; A61N 2005/1055; A61N 2005/1074; A61B 5/055; G01R 33/385; G01R 33/50
See application file for complete search history.

(56) References Cited

U.S. PATENT DOCUMENTS

| | | |
|---|---|---|
| 4,680,548 A | 7/1987 | Edelstein |
| 4,774,468 A | 9/1988 | Bydder |
| 4,812,761 A | 3/1989 | Vaughan, Jr. |
| 4,831,330 A | 5/1989 | Takahashi |

(Continued)

FOREIGN PATENT DOCUMENTS

| | | |
|---|---|---|
| CN | 1969194 A | 5/2007 |
| CN | 101438959 A | 5/2009 |

(Continued)

OTHER PUBLICATIONS

International Search Report issued in corresponding international application No. PCT/US2014/024354 mailed Jun. 12, 2014.

(Continued)

*Primary Examiner* — Alexei Bykhovski
(74) *Attorney, Agent, or Firm* — Davis Graham & Stubbs LLP

(57) ABSTRACT

Systems, methods, and computer software relating to gating using non-parallel imaging planes, determining accumulated dose to tissues during radiotherapy with actual beam delivery information, stopping/adjusting/reoptimizing therapy based on such accumulated doses and the generation and use of prognostic motion models and prognostic-motion adapted radiation treatment plans are disclosed.

23 Claims, 13 Drawing Sheets

(56) References Cited

U.S. PATENT DOCUMENTS

| | | |
|---|---|---|
| 5,184,076 A | 2/1993 | Ehnholm |
| 5,477,146 A | 12/1995 | Jones |
| 5,565,778 A | 10/1996 | Brey |
| 5,594,342 A | 1/1997 | Brey |
| 5,619,140 A | 4/1997 | Brey |
| 5,621,323 A | 4/1997 | Larsen |
| 5,990,681 A | 11/1999 | Richard |
| 6,060,882 A | 5/2000 | Doty |
| 6,100,694 A | 8/2000 | Wong |
| 6,177,797 B1 | 1/2001 | Srinivasan |
| 6,198,957 B1 | 3/2001 | Green |
| 6,316,941 B1 | 11/2001 | Fujita |
| 6,366,798 B2 | 4/2002 | Green |
| 6,369,570 B1 | 4/2002 | Wong |
| 6,396,271 B1 | 5/2002 | Burl |
| 6,420,871 B1 | 7/2002 | Wong |
| 6,624,632 B2 | 9/2003 | Iriguchi |
| 6,930,480 B1 | 8/2005 | Fujita |
| 7,084,629 B2 | 8/2006 | Monski, Jr. |
| 7,221,161 B2 | 5/2007 | Fujita |
| 7,268,554 B2 | 9/2007 | Vaughan |
| 7,282,915 B2 | 10/2007 | Giaquinto |
| 7,397,246 B2 | 7/2008 | Freytag |
| 7,855,559 B2 | 12/2010 | DeFranco |
| 7,907,987 B2 | 3/2011 | Dempsey |
| 7,911,209 B2 | 3/2011 | Alradady |
| 8,022,705 B2 | 9/2011 | Bogdanov |
| 8,035,384 B2 | 10/2011 | Saha |
| 8,129,992 B2 | 3/2012 | Cork |
| 8,217,653 B2 | 7/2012 | Vaughan |
| 8,331,531 B2 | 12/2012 | Fahrig |
| 8,427,158 B2 | 4/2013 | Huish |
| 8,497,682 B2 | 7/2013 | Huish |
| 8,704,520 B2 | 4/2014 | Saha |
| 8,710,843 B2 | 4/2014 | Carlone |
| 9,404,983 B2 | 8/2016 | Dempsey |
| 9,664,763 B2 | 5/2017 | Amthor |
| 10,107,878 B2 | 10/2018 | Habara |
| 10,456,595 B2 * | 10/2019 | Ribbing ............... A61N 5/1071 |
| 10,466,319 B2 | 11/2019 | Dempsey |
| 2001/0001807 A1 | 5/2001 | Green |
| 2003/0071621 A1 | 4/2003 | Watkins |
| 2003/0122546 A1 | 7/2003 | Leussler |
| 2003/0146750 A1 | 8/2003 | Thomas |
| 2003/0193380 A1 | 10/2003 | De Swiet |
| 2004/0140808 A1 | 7/2004 | Thomas |
| 2005/0062472 A1 | 3/2005 | Bottomley |
| 2005/0099179 A1 | 5/2005 | Monski, Jr. |
| 2005/0231201 A1 | 10/2005 | Fujimoto |
| 2006/0033497 A1 | 2/2006 | Chmielewski |
| 2006/0033501 A1 | 2/2006 | Vaughan, Jr. |
| 2006/0273795 A1 | 12/2006 | Rieke |
| 2007/0007964 A1 | 1/2007 | Vaughan, Jr. |
| 2007/0016003 A1 | 1/2007 | Piron |
| 2007/0159170 A1 | 7/2007 | Freytag |
| 2007/0216409 A1 | 9/2007 | Overweg |
| 2007/0247158 A1 | 10/2007 | Nistler |
| 2007/0247160 A1 | 10/2007 | Vaughan, Jr. |
| 2008/0088309 A1 | 4/2008 | Eberler |
| 2008/0094063 A1 | 4/2008 | Renz |
| 2008/0100297 A1 | 5/2008 | Ishii |
| 2008/0129296 A1 | 6/2008 | Fischer |
| 2008/0275332 A1 | 11/2008 | Alradady |
| 2008/0278167 A1 | 11/2008 | Vaughan, Jr. |
| 2008/0306377 A1 | 12/2008 | Piron |
| 2009/0009169 A1 | 1/2009 | Schulz |
| 2009/0021256 A1 | 1/2009 | Soutome |
| 2009/0134873 A1 | 5/2009 | Cho |
| 2009/0134875 A1 | 5/2009 | Tomiha |
| 2009/0149735 A1 | 6/2009 | Fallone |
| 2009/0237077 A1 | 9/2009 | Vaughan |
| 2010/0033185 A1 | 2/2010 | Saha |
| 2010/0079139 A1 | 4/2010 | Defranco |
| 2010/0094119 A1 * | 4/2010 | Yu ........................ A61B 6/022 600/1 |
| 2010/0102811 A1 | 4/2010 | Demas |
| 2010/0164494 A1 | 7/2010 | Koretsky |
| 2010/0239066 A1 | 9/2010 | Fahrig |
| 2010/0253333 A1 | 10/2010 | Zhai |
| 2010/0253338 A1 | 10/2010 | Eryaman |
| 2010/0253350 A1 | 10/2010 | Huish |
| 2010/0253351 A1 | 10/2010 | Huish |
| 2011/0012593 A1 | 1/2011 | Shvartsman |
| 2011/0043207 A1 | 2/2011 | Gross |
| 2011/0125005 A1 | 5/2011 | Misic |
| 2011/0166437 A1 | 7/2011 | Chang |
| 2011/0215807 A1 | 9/2011 | Misic |
| 2012/0146643 A1 | 6/2012 | Saha |
| 2012/0150017 A1 | 6/2012 | Yamaya |
| 2012/0184841 A1 | 7/2012 | Nielsen |
| 2012/0268132 A1 | 10/2012 | Zhu |
| 2012/0286786 A1 | 11/2012 | Schellekens |
| 2012/0286921 A1 | 11/2012 | Wang |
| 2013/0027040 A1 | 1/2013 | Alagappan |
| 2013/0035584 A1 | 2/2013 | Fahrig |
| 2013/0131433 A1 | 5/2013 | Katscher |
| 2013/0165770 A1 | 6/2013 | Li |
| 2014/0043027 A1 | 2/2014 | Overweg |
| 2014/0074076 A1 * | 3/2014 | Gertner ................ A61B 6/12 606/169 |
| 2014/0084926 A1 | 3/2014 | Amthor |
| 2014/0125339 A1 | 5/2014 | Lee |
| 2014/0128719 A1 | 5/2014 | Longfield |
| 2014/0167758 A1 | 6/2014 | Sambandamurthy |
| 2014/0191757 A1 | 7/2014 | Randell |
| 2014/0221816 A1 | 8/2014 | Franke |
| 2014/0253126 A1 | 9/2014 | Habara |
| 2014/0266206 A1 | 9/2014 | Dempsey |
| 2014/0275962 A1 | 9/2014 | Foo |
| 2015/0054506 A1 | 2/2015 | Eberler |
| 2015/0112187 A1 | 4/2015 | Petropoulos |
| 2015/0177346 A1 | 6/2015 | Mazurewitz |
| 2015/0217136 A1 | 8/2015 | Stanescu |
| 2016/0146911 A1 | 5/2016 | Chmielewski |
| 2016/0216344 A1 | 7/2016 | Habara |
| 2017/0299671 A1 | 10/2017 | Holle |
| 2017/0307704 A1 | 10/2017 | Leussler |
| 2018/0299520 A1 * | 10/2018 | Piron ..................... A61B 5/055 |
| 2018/0345042 A1 * | 12/2018 | Voronenko ........... A61N 5/1081 |
| 2019/0091487 A1 * | 3/2019 | Pal ....................... A61N 5/1067 |
| 2019/0310330 A1 | 10/2019 | Yang |
| 2019/0353724 A1 | 11/2019 | Snelten |
| 2020/0041587 A1 | 2/2020 | Findeklkee |
| 2021/0201475 A1 * | 7/2021 | Bose ..................... G06T 7/0014 |
| 2021/0302514 A1 | 9/2021 | Yang |
| 2022/0120831 A1 | 4/2022 | Yang |
| 2022/0314025 A1 * | 10/2022 | Zhang ................... A61N 5/1084 |
| 2023/0225629 A1 * | 7/2023 | Lee ....................... A61B 5/1127 600/300 |

FOREIGN PATENT DOCUMENTS

| | | |
|---|---|---|
| CN | 102711915 A | 10/2012 |
| CN | 102713682 A | 10/2012 |
| EP | 2345906 A1 | 7/2011 |
| EP | 2523011 A1 | 11/2012 |
| EP | 2589976 | 5/2013 |
| GB | 2424281 A | 9/2006 |
| JP | 2002102207 | 4/2002 |
| JP | 2009142646 A | 8/2009 |
| JP | 2012511382 | 5/2012 |
| JP | 2012236018 A | 12/2012 |
| KR | 20170116070 | * 10/2017 |
| WO | 2005124379 A1 | 12/2005 |
| WO | WO2007046910 | * 4/2007 |
| WO | 2008122899 A1 | 10/2008 |
| WO | 2009013650 A2 | 1/2009 |

(56) References Cited

FOREIGN PATENT DOCUMENTS

| WO | 2011063342 A1 | 5/2011 |
|---|---|---|
| WO | 2011148278 | 12/2011 |

OTHER PUBLICATIONS

PCT/IB2022/057231 International Search Report and Written Opinion dated Nov. 14, 2022 (11 pages).

* cited by examiner (410) Acquiring real-time images of a patient from a magnetic resonance imaging system in at least two non-parallel planes (420) Contouring an anatomical structure of the patient in the at least two non-parallel planes (430) Setting spatial limits for movement of the anatomical structure in the at least two non-parallel planes (440) Controlling a radiotherapy device to deliver a radiotherapy beam to the patient (450) Gating off the radiotherapy beam when the anatomical structure exceeds a spatial limit in either of the at least two non-parallel planes.

FIG. 4

(610) Delivering radiotherapy to a patient from a radiotherapy device (620) Acquiring images of the patient from a magnetic resonance imaging system during radiotherapy (630) Acquiring actual beam delivery information during radiotherapy, the actual beam delivery information comprising actual beam measurements including one or more of: measured monitor units, measured MLC leaf positions, measured gantry positions, measured couch positions and measured fluence profiles (640) Calculating dose to tissues during the radiotherapy based on the acquired images and the acquired actual beam delivery information (650) Accumulating dose to tissues during the radiotherapy

FIG. 6

(910) Acquiring pre-treatment images with a magnetic resonance imaging system, the pre-treatment images capturing movement of a patient (920) Generating a prognostic motion model based on at least the pre-treatment images (930) Generating a prognostic motion adapted radiation treatment plan based at least on the prognostic motion model

FIG. 9

(1110) Acquiring treatment images of a patient from a magnetic resonance imaging system, the treatment images capturing movement of a patient (1120) Delivering radiotherapy to the patient from a radiotherapy device according to a prognostic motion adapted radiation treatment plan based at least on a prognostic motion model

FIG. 11

(1310) acquiring actual beam delivery information during radiotherapy, the actual beam delivery information comprising actual beam measurements (1320) calculating dose to tissues during the radiotherapy based on the acquired images and the acquired actual beam delivery information (1330) accumulating dose to tissues during the radiotherapy (1340) generating a second prognostic motion adapted radiation treatment plan if the accumulated dose to an anatomical structure exceeds a specified limit (1350) continuing the delivery of radiotherapy utilizing the second prognostic motion adapted radiation treatment plan

FIG. 13

MRI GUIDED RADIOTHERAPY

RELATED APPLICATION(S)

This application claims priority to and the benefit of U.S. Provisional Application No. 63/270,862, filed Oct. 22, 2021, titled "MRI Guided Radiotherapy," which is hereby incorporated by reference.

DESCRIPTION OF THE RELATED ART

Magnetic resonance imaging (MRI), or nuclear magnetic resonance imaging, is a noninvasive imaging technique that uses the interaction between radio frequency pulses, a strong magnetic field (modified with weaker gradient fields applied across it for encoding) and body tissue to obtain projections, spectral signals, and images of planes or volumes from within a patient's body. Magnetic resonance imaging is particularly helpful in the imaging of soft tissues and may be used for the diagnosis of disease. Real-time or cine MRI may be used for the diagnosis of medical conditions requiring the imaging of moving structures within a patient. Real-time MRI may also be used in conjunction with interventional procedures, such as radiation therapy or image guided surgery, to help guide such procedures.

SUMMARY

Systems, methods, and computer software relating to gating using non-parallel imaging planes, determining accumulated dose to tissues during radiotherapy utilizing actual beam delivery information, and the generation and use of prognostic motion models and prognostic-motion adapted radiation treatment plans are disclosed. In one aspect, systems and software can be configured to perform operations including acquiring real-time images of a patient from a magnetic resonance imaging system in at least two non-parallel planes and contouring an anatomical structure of the patient in the at least two non-parallel planes. Spatial limits can be set for movement of the anatomical structure in the non-parallel planes. A radiotherapy device can be controlled to deliver a radiotherapy beam to the patient and the radiotherapy beam can be gated off when the anatomical structure exceeds a spatial limit in either of the non-parallel planes. In some variations, there can be three orthogonal planes and the contouring of the anatomical structure(s) of the patient can be performed via machine autocontouring.

In other variations, the radiotherapy device can be further controlled to deliver stereotactic radiosurgery (SRS) to the patient. The magnetic resonance imaging system can operate at a field strength of less than 1.0 Tesla, and spatial limits can be set within 0.5 mm of the boundaries of the anatomical structure in at least two non-parallel planes.

In a related aspect, systems and software can be configured perform operations including delivering radiotherapy to a patient from a radiotherapy device, images of the patient can be acquired from a magnetic resonance imaging system during the radiotherapy, and actual beam delivery information can be acquired during the radiotherapy. The actual beam delivery information can include actual beam measurements including one or more of: measured monitor units, measured MLC leaf positions, measured gantry positions, measured couch positions and measured fluence profiles. Dose to tissues can be calculated during the radiotherapy based on the acquired images and the acquired actual beam delivery information. The dose can also be accumulated to tissues during the radiotherapy. In some variations, the accumulated dose can be displayed in three orthogonal planes.

In other variations, an anatomical structure of the patient can be contoured. Accumulated dose to a contoured anatomical structure can be determined and a notification or alarm can be provided if the accumulated dose to the contoured anatomical structure exceeds a specified limit. Delivery of radiotherapy can be stopped if the accumulated dose to the contoured anatomical structure exceeds the specified limit and a reoptimized treatment plan can be determined.

In another interrelated aspect, pre-treatment images can be acquired with a magnetic resonance imaging system, the pre-treatment images capturing movement of a patient. A prognostic motion model can then be generated based on at least the pre-treatment images and a prognostic motion adapted radiation treatment plan can be generated based at least on the prognostic motion model.

In some variations, the prognostic motion model can include a model of expected patient movement during treatment. The prognostic motion model can also be generated to include multiple types of motion observed in the pre-treatment images such as regular motion due to breathing, motion due to deep breathing, motion due to GI system gas movement, motion due to bladder filling, motion due to patient movement, motion due to swallowing, chest-wall breathing, diaphragm breathing, talking, eye movement, cardiac motion, or voluntary muscle motion.

In other variations, the prognostic motion adapted radiation treatment plan can take into account the prognostic motion model's expected patient movement during treatment including the deformation of a target or an organ of interest.

The prognostic motion adapted radiation treatment plan can be configured to adjust or stop delivery when an irregular patient movement of the prognostic motion model is observed during treatment. In other variations, the prognostic motion adapted radiation treatment plan can aim the radiation beam where the target is expected to be based on the prognostic motion model and the system latency rather than to a specific point in space.

During radiotherapy, treatment images of a patient can be acquired from a magnetic resonance imaging system, the treatment images capturing movement of a patient. Radiotherapy can then be delivered to the patient from a radiotherapy device according to a prognostic motion adapted radiation treatment plan based at least on a prognostic motion model. In some variations, the delivery of radiotherapy can be interrupted when the movement of the patient does not match an expected patient movement. In other variations, a second prognostic motion model can be generated utilizing the acquired treatment images. A second prognostic motion adapted radiation treatment plan can be generated based at least on the second prognostic motion model and the delivery of radiotherapy can be resumed utilizing the second prognostic motion adapted radiation treatment plan.

In still other variations, combining the techniques described herein, actual beam delivery information can be acquired during the radiotherapy and dose to tissues during the radiotherapy can be calculated based on the acquired images and the acquired actual beam delivery information. Dose to tissues can be accumulated during the radiotherapy and a second prognostic motion adapted radiation treatment plan can be generated if the accumulated dose to an anatomical structure exceeds a specified limit. The delivery of radiotherapy can be continued utilizing the second prognostic motion adapted radiation treatment plan. The second prognostic motion adapted radiation treatment plan can also be generated taking into account the accumulated dose and account for any under dosage or over dosage.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 illustrates one embodiment of a process for gating a radiotherapy beam consistent with certain aspects of the present disclosure.

FIG. 6 illustrates one embodiment of a process for use with systems and software for calculating an accumulated radiation dose utilizing actual beam delivery information consistent with certain aspects of the present disclosure.

FIG. 9 illustrates the generation of a prognostic motion model and prognostic motion adapted radiation treatment plan consistent with certain aspects of the present disclosure.

FIG. 11 illustrates one embodiment of a process for delivering radiotherapy according to a prognostic motion adapted radiation treatment plan consistent with certain aspects of the present disclosure.

FIG. 13 illustrates an exemplary process for reoptimizing a prognostic motion adapted radiation treatment plan based on accumulated dose calculation consistent with certain aspects of the present disclosure.

DETAILED DESCRIPTION

The present disclosure provides improvements to the delivery of therapeutic radiation by improved tissue tracking and treatment gating. Also disclosed are improvements to radiation dose calculation and accumulation through, among other things, determining the actual dose of radiation delivered to a patient during the course of radiation treatment. Further disclosed are techniques utilizing prognostic patient motion models that allow for the creation of prognostic motion adapted radiation treatment plans and further improved radiation delivery utilizing such plans.

Figure 1:
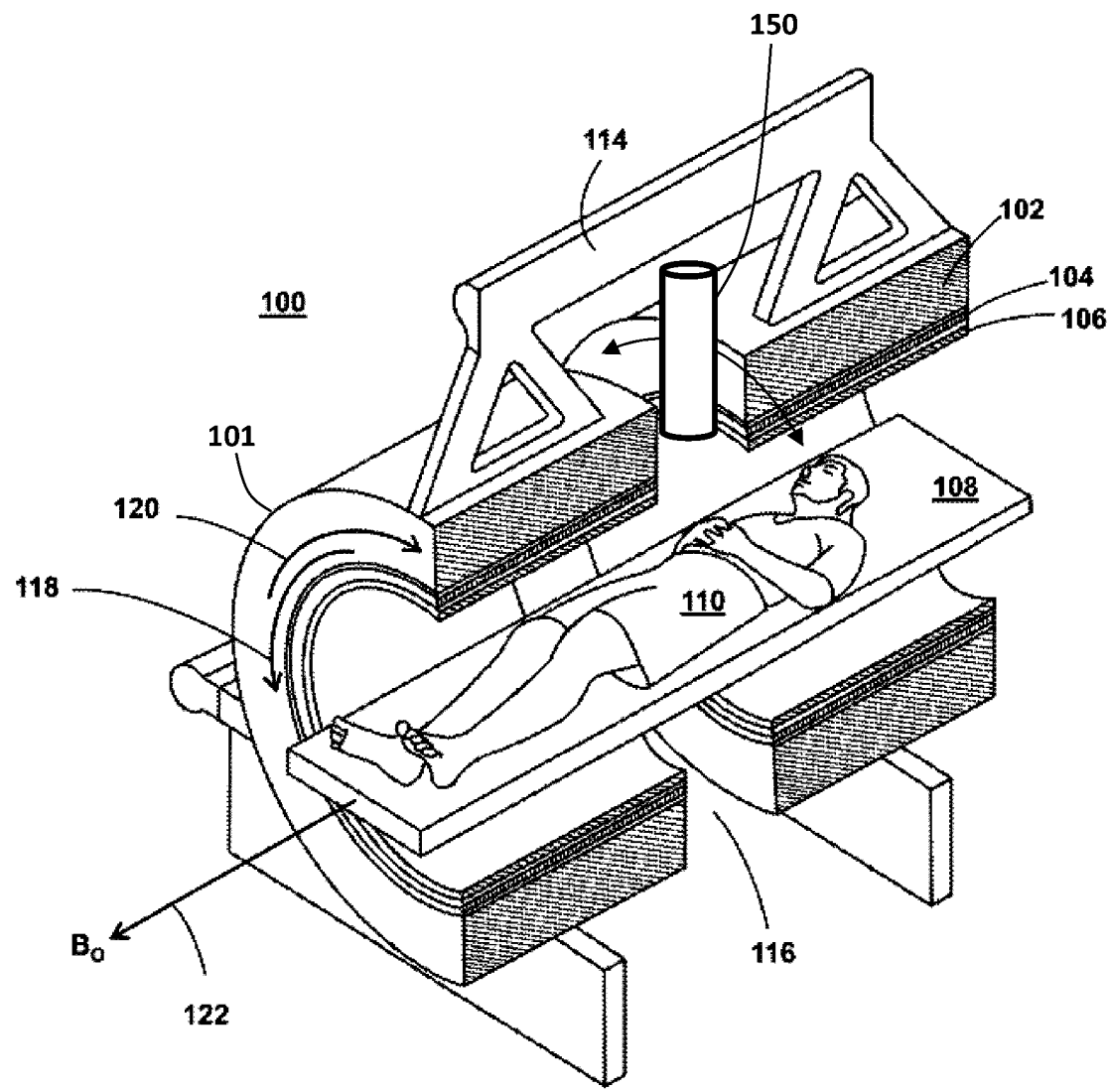
FIG. 1 illustrates one implementation of a magnetic resonance guided radiotherapy (MRgRT) system that combines a magnetic resonance imaging system (MRI) and a radiotherapy source consistent with certain aspects of the present disclosure.

FIG. 1 illustrates one implementation of a magnetic resonance guided radiotherapy system 100 (MRgRT system) that combines a magnetic resonance imaging system (MRI) 101 and a radiotherapy source 150 consistent with certain aspects of the present disclosure. In FIG. 1, MRI 101 includes a main electromagnet 102, a gradient coil assembly 104 and an RF coil system 106. Within MRI 101 is a patient couch 108 on which a patient 110 may lie.

The exemplary main electromagnet 102 of MRI 101 can be a gapped solenoidal electromagnet separated by buttresses 114 with a gap 116 as shown in FIG. 1. A "gap," as the term is used herein, refers to the type of solenoidal magnet gap 116 depicted in FIG. 1. As also depicted in FIG. 1, the currents in the main electromagnet 102 may be in either a first direction 118 or a second direction 120, to generate the main magnetic field $B_0$, shown along axis 122, where the direction of the field is dependent on the main electromagnet current direction.

Figure 5:
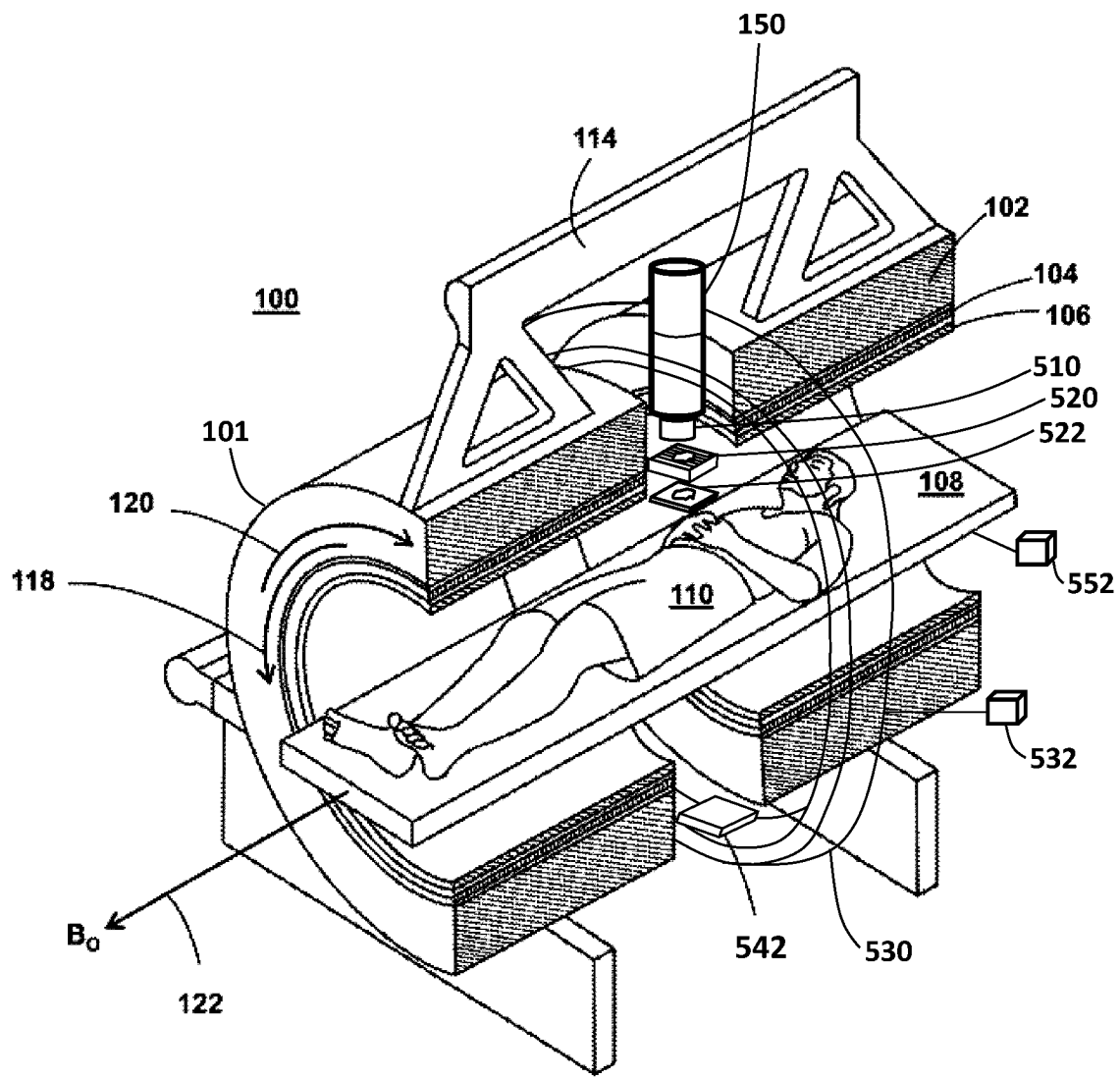
FIG. 5 illustrates an MRgRT system including exemplary mechanisms for the acquisition of actual beam delivery information consistent with certain aspects of the present disclosure.

FIG. 1 also depicts a simplified exemplary radiotherapy device 150 for the delivery of radiation therapy. Examples of radiotherapy devices can include, for example, linear accelerators (linacs) for the delivery of high energy photons (x-rays, gamma rays, etc.), particle beam sources (e.g., proton, heavy-ion, neutron, electron, etc.), etc. Radiotherapy device 150 can be configured to move to different locations about the patient to deliver radiation at a variety of angles. For example, the radiotherapy device can be mounted on a rotatable gantry disposed between the MRI magnet halves such that the gantry can rotate about the patient to allow imaging with the MRI while delivering radiation at varying gantry angles. A simplified depiction of a rotatable gantry is shown in FIG. 5. In other embodiments, radiotherapy device 150 can be mounted on a robotic arm or may be at a fixed position.

As used herein, the phrase "MRgRT system" refers to the hardware and/or software associated with the operation of the magnetic resonance imaging system and the radiotherapy device. In contrast, the more general phrase "system" used throughout the present disclosure encompasses any hardware and/or software required for effecting the disclosed concepts referring to that system. For example, while the MRgRT system can deliver radiotherapy and perform imaging, it may not necessarily be able to cause the analysis or display of data as described in certain embodiments herein. Thus, use of the term "a/the system" encompasses processors and/or computer programs (as well as the MRgRT system, as needed) to enable the disclosed concepts, for example, radiotherapy gating, dose calculation, radiation treatment plan generation, etc. While FIG. 1 depicts an exemplary system, the improvements to MRI-guided therapy disclosed herein may be implemented with other MRgRT designs.

Figure 2:
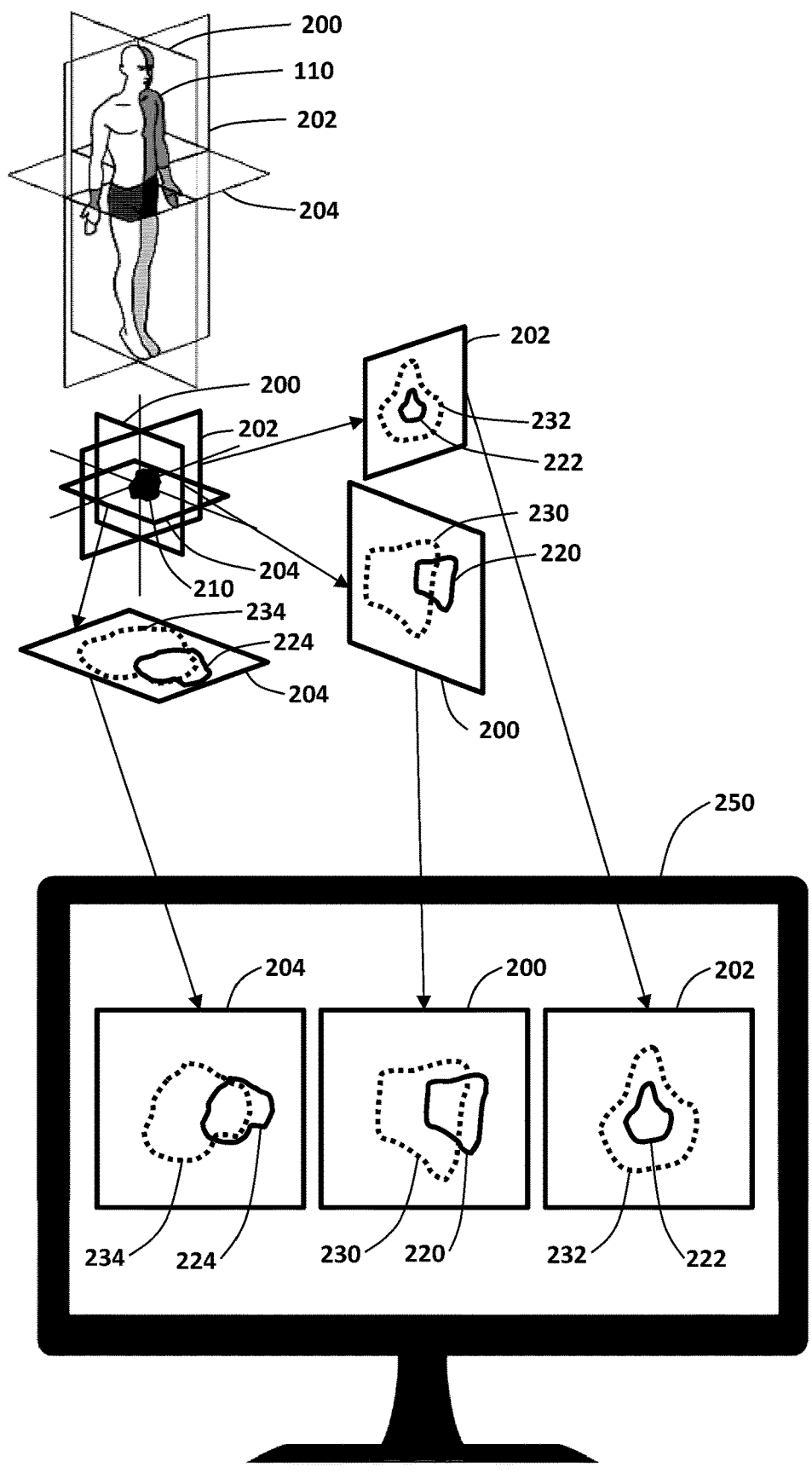
FIG. 2 illustrates an exemplary implementation of multi-planar patient imaging by an MRgRT system utilizing non-parallel imaging planes consistent with certain aspects of the present disclosure.

FIG. 2 illustrates an example of patient imaging by an MRgRT system utilizing non-parallel imaging planes consistent with certain aspects of the present disclosure. Imaging can be performed in varying planes through the patient to provide different views of patient anatomy that may be utilized for diagnosis, radiation delivery, etc. FIG. 2 depicts three exemplary non-parallel planes through the patient 110 (e.g., a sagittal plane 200, a coronal plane 202, and a transverse plane 204). In some embodiments, such planes may correspond to natural coordinate systems for the particular system (e.g., having a dimension along the main magnetic field axis or transverse to the axis), though this is not required and any orientation of the disclosed planes is contemplated. Depicted below the patient is an inset illustrating an exemplary anatomical structure (e.g., a target tumor) 210 being imaged, generally centered at the intersection of the exemplary non-parallel planes.

As depicted in the further inset, the 3D anatomical structure 210 has 2D projections (220, 222, 224) imaged in the corresponding non-parallel planes (200, 202, 204). Such projections may be utilized to facilitate the delivery or gating of radiation with respect to certain spatial limits (e.g., 230, 232, 234), which are depicted in FIG. 2 by the dashed boundaries. Also, in certain embodiments, the system can cause a display device 250 to display graphical representations of any combination of the non-parallel planes, projections of anatomical structures, spatial limits, etc. Examples of display devices can include computer monitors, touchscreen monitors, smart phone screens, etc.

As shown in the example of FIG. 2, some embodiments can include three orthogonal planes. More generally, advantages can be obtained when the system is configured to image in at least two non-parallel planes. In some embodiments, the non-parallel planes can be orthogonal, as shown. In other embodiments, the non-parallel planes can be oblique (i.e., not orthogonal). It is contemplated that combinations of the above can be utilized. For example, in an embodiment with three planes, there can be a coronal plane and a sagittal plane that are orthogonal in addition to a third plane (e.g., similar to a transverse plane) that is oblique to either one or both of the other two planes. In general, the terms ("orthogonal" and "oblique") are used to describe the relationship of the planes to one another and not to any particular coordinate system. Further details of the embodiment and concepts disclosed in FIG. 2 are discussed below with reference to the contouring/gating embodiments discussed with respect to FIG. 4.

Figure 3:
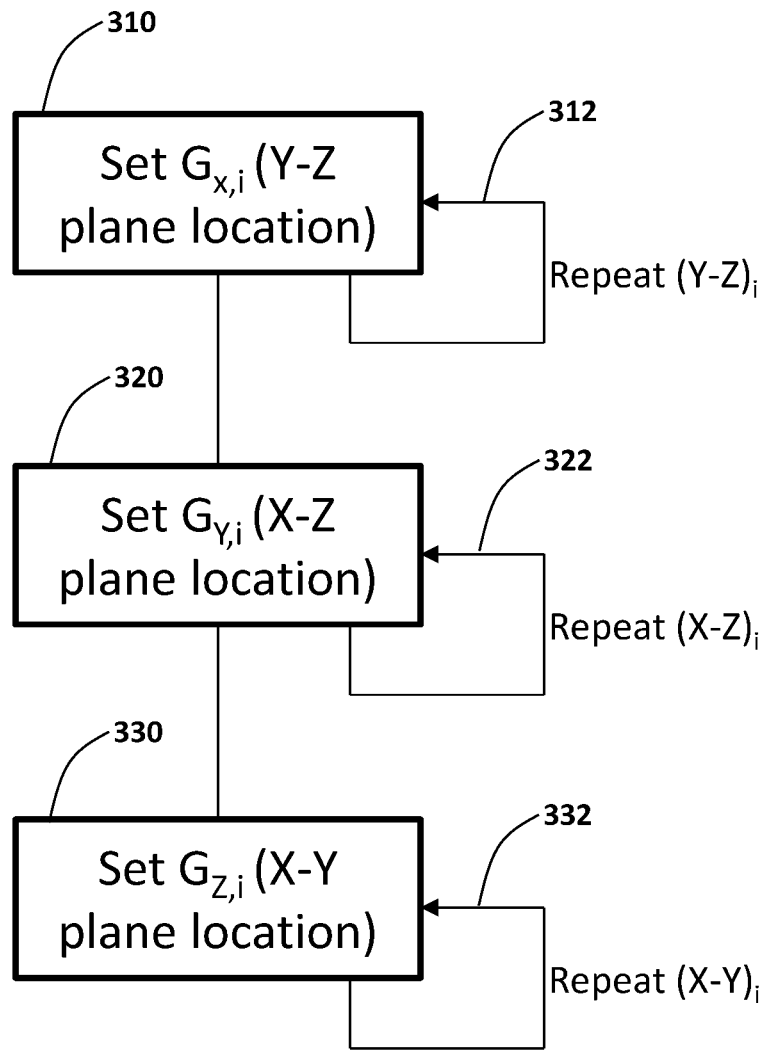
FIG. 3 illustrates an embodiment of a process for performing non-parallel planar imaging in accordance with certain aspects of the present disclosure.

FIG. 3 illustrates an embodiment of a process for performing non-parallel planar imaging in accordance with certain aspects of the present disclosure. The use of multiple non-parallel planes can be enabled by, for example, energizing and controlling various subsystems of the gradient coil system of the MRI. As depicted by the exemplary process in FIG. 3, at 310, a portion of the Y-Z plane can be imaged with the establishment of a gradient field in the X direction by the X gradient coils. Then, at 320, a portion of the X-Z plane can be imaged with the establishment of a gradient field in the Y direction by the Y gradient coils. At 330, a portion of the X-Y plane can be imaged with the establishment of a gradient field in the Z direction by the Z gradient coils.

In some embodiments, such as for volumetric imaging applications, multiple images can be acquired in offset planes (e.g., repeatedly imaging a plane in different gradient coil configurations to shift the location of slice selection). FIG. 3 depicts a process for imaging the i-th plane (e.g., there being N total planes with the instant plane being imaged designated with the subscript (i)) by the process loops (312, 322, 332) associated with each respective gradient coil. The present disclosure contemplates that such can be done in any combination, for example, the plane orientation can be changed in sequence (e.g., Y-Z, then X-Z, then X-Y) and then offsets applied to acquire a new set of non-parallel images (e.g., Y-Z+$\Delta$X, then X-Z+$\Delta$Y, then X-Y+$\Delta$Z).

Accordingly, the present disclosure contemplates that any combination of X, Y, and Z gradient coils can be energized (including multiple coils at the same time such as X and Y). Such use of the gradient coil system can allow rapid sequences of imaging to be obtained by switching between imaging planes. This rapid switching can thus allow the acquiring of the real-time images from the magnetic resonance imaging system in at least two non-parallel planes.

In some implementations, orthogonal acquisitions can be performed as separate imaging plane groups (e.g., sagittal, coronal, or transverse) that may each include one or more imaging planes through the patient. For example, in an embodiment there may be a single imaging plane for each group (e.g., three planes total). In other embodiments, there may be multiple planes in each group (e.g., 10 parallel planes per non-parallel group for 30 total planes) that can facilitate volumetric imaging. The system (optionally based on user input) can set the imaging plane orientation (sagittal, coronal, or transverse) and imaging plane offset (e.g., X, Y, Z, coordinates) independently. In some embodiments, the system can set the phase encoding direction based on slice orientation for best image quality and speed. Also, in some embodiments, other parameters can be common between the imaging plane groups allowing for rapid switching between orientations. Imaging speed can be enhanced in some embodiments by using a combination of acceleration (e.g., GeneRalized Autocalibrating Partially Parallel Acquisitions (GRAPPA) and partial Fourier) in the phase encoding direction. Also, image quality can be improved by incorporating phase oversampling when necessary to prevent aliasing. Thus, the system can perform image analysis to detect the presence of aliasing and implement phase oversampling to reduce or prevent such.

The system can perform various types of MRI to allow a more accurate discerning of patient anatomy. In some embodiments, for example, the acquiring of the real-time images from the magnetic resonance imaging system in at least two non-parallel planes can include T1 and T2 weighted volumetric scans at an SRS isocenter. Other types of planar or volumetric scans can also be implemented by the disclosed MRI.

FIG. 4 illustrates one embodiment of a process for gating a radiotherapy beam consistent with certain aspects of the present disclosure. At 410, the system can acquire real-time images of a patient from a magnetic resonance imaging system in at least two non-parallel planes. At 420, the system can contour an anatomical structure of the patient in the non-parallel planes. At 430, the system can set spatial limits for movement of the anatomical structure in the non-parallel planes. At 440, the system can control a radiotherapy device to deliver a radiotherapy beam to the patient. At 450, the system can gate off the radiotherapy beam when the anatomical structure exceeds a spatial limit in either of the non-parallel planes.

As used herein, "real-time" means with minimal delay between image data capture and image development. In particular, the acquisition, reconstruction, and processing time can be less than the frame rate so that the imaging can keep pace with the procedure. In this way, the utilization of such real-time images can inform the clinician or the system about the nearly current state of the patient. In practice, implementations of real-time imaging can involve delays of less than one second and sometimes much less, e.g., 0.25 seconds to reconstruct and display a volumetric image. The required frame rate can depend on the speed of the motions being tracked in the patient, with 0.25 seconds being sufficient to resolve typical cardiac and respiratory motions.

With reference to operation 420, in some embodiments, the contouring of the anatomical structure of the patient can be performed via machine autocontouring. For example, from the MRI images, the system can perform image analysis (e.g., using gradient analysis or other edge-detection algorithms) to detect edges of anatomical structures and generate contours around the detected edges to isolate and identify the anatomical structures. In other embodiments, the contouring of the anatomical structure of the patient can be performed via a machine receiving manual user input. For example, a clinician can receive patient images at a computing device and via various input methods such as a mouse, touchscreen, stylus, etc., generate or edit contours around various anatomical structures. In yet other embodiments, the two methods can be combined, to allow the clinician to add, remove, or edit machine-generated contours. Deformable image registration concepts can also be utilized to facilitate contouring in multiple images in conjunction with both the machine autocontouring and manual user input concepts. For example, a contour in a prior image can be deformably registered onto a current image. While the present disclosure often refers to a tumor or object intended to receive radiation as a "target," such is also considered as being an "anatomical structure" that may be contoured and tracked by the MRgRT system.

With reference to operation 450, gating (e.g., the stopping of delivery of radiation) can be utilized by the system, for example, when needed to protect the patient from receiving an improper radiation dose. Such gating can occur, for example, when the system determines that radiation is not being delivered properly due to movement of the patient or target or an analysis of the delivered radiation dose.

To facilitate gating functionality, spatial limits around an anatomical structure can be established by the system or by a clinician where, if the anatomical structure exceeds one or more spatial limits, the system may gate. Simplified depictions of spatial limits (230, 232, 234) are illustrated in FIG. 2 by the dashed lines in the individual planes (200, 202, 204) where the planar projections (220, 222, 224) of the anatomical structure can be tracked by the system. In the example shown, the spatial limits are depicted as an expanded region around the anatomical structure and represent permissible regions for delivering radiation. In the example, the anatomical structure is depicted as being shifted such that the projections of the anatomical structure in two (200, 204) of the non-parallel planes are outside their respective spatial limits (230, 234). Accordingly, the system can identify this as meeting a gating condition and suspend delivery of radiation. In some embodiments, the margins defining the spatial limits can be set to zero or near zero to essentially conform to the contour of the anatomical structure. In other embodiments, the spatial limit can be set in the system as a percentage increase around the volume of the anatomical structure (e.g., 1%, 2%, 5%, etc.), a specific distance (e.g., a 0.1 mm margin, 0.2 mm margin, etc.), etc.

In some embodiments, the system can be configured to allow a spatial limit to be violated for a limited period of time without gating, for example, to permit brief motions that do not have an excessive effect on the radiation dose. For example, in varying embodiments the spatial limit may be exceeded for up to 0.1 seconds, 0.25 seconds 0.5 seconds, or 1.0 seconds. In other embodiments, certain anatomical structures (e.g., the prostate) can be allowed to exceed the spatial limit for 10s of seconds, e.g., 10, 20, or 30 seconds. In further embodiments, the determination of the period for which a spatial gate can be violated may be determined by the system based on the permissible dose to nearby anatomical structures that may drift into the radiation beam when the target moves.

While the present disclosure contemplates that imaging using multiple planes can be performed in any location of a patient, there are specific applications that benefit from the accuracy that the disclosed multiplane imaging/gating provides. One example of such an application is stereotactic radiosurgery (SRS), which is typically utilized to treat a cranial region of the patient (e.g., brain tumors). Conventional SRS often involves physically securing the patient by mechanically clamping the patient's head into a fixed position. Despite such techniques, the internal anatomy of the patient can be connected to (or be) soft tissue. Thus, radiation targets may still move relative to the mechanically clamped skull of the patient, for example, when the patient yawns, coughs, shifts, etc. Because conventional SRS assumes that the patient's anatomy is static (or merely tracks skull displacements assuming that the anatomy rigidly moves with it), the actual movement of internal soft tissues during treatment may be unknown and thereby cause the improper delivery of radiation dose.

The techniques and radiotherapy systems disclosed herein can be particularly well-suited to perform SRS and, as such, the systems can be controlled to deliver stereotactic radiosurgery to the patient. Because brain tumors are quite small and the margin of error also small, the treatment of tumors in SRS can involve delivering very small (e.g., in cross-section) beams of radiation. In some cases, such delivery can be facilitated by the use of high-resolution multi leaf collimators to provide highly conformal radiotherapy to very small targets. Also, due to the possible need to gate radiation quickly while respecting exacting tolerances for the delivery of radiation, multiplanar, non-parallel tracking/gating can be combined with delivery of small beam radiation to deliver highly precise conformal radiotherapy during an SRS procedure. Highly accurate delivery of radiation can be further facilitated by a system utilizing a magnetic resonance imaging system at a field strength of less than 2.0, 1.0. 0.75, 0.5 or 0.35 Tesla. Operating the MRI at such comparatively low magnetic fields (e.g., compared to high-field MRI which can be 3.5 T or higher), can permit imaging with reduced artifact production and thus permit more spatially accurate representations of anatomical structures in the MRI images.

In other embodiments that may be utilized with SRS, the system can be configured to set spatial limits within 0.5 mm of the boundaries of the anatomical structure in at least two non-parallel planes. Other examples of similarly conformal spatial limits can include 0.1, 0.25, 0.75, or 1.0 mm, etc.

FIG. 5 illustrates an MRgRT system including a multileaf collimator (MLC) 520 for collimating the beam into a specific shape during treatment. Exemplary systems can also include mechanisms for the acquisition of actual beam delivery information. For example, some embodiments can include a beam output sensor 510 (e.g., a monitor/ion chamber). In addition, the shape of the beam (or positions of the MLC leaves) can be measured by a beam shape sensor or fluence sensor 522 (e.g., a scintillator). The MRgRT system can include a gantry 530 that can include gantry sensors 532 to measure gantry angle/position. There may also be an exit radiation detector 542 that may be mounted to rotate with gantry to measure the radiation not absorbed or scattered by the patient (e.g., an electronic portal imaging device or EPID). Also, patient couch 108 can include a patient couch sensor 552 to measure the location/orientation of the patient couch during treatment. The present disclosure contemplates that the described sensors are exemplary and that such may be incorporated in any combination in an MRgRT system. Also, the examples given are not exclusive of other sensors that may be incorporated into the system to provide actual beam delivery information. Exemplary types and use of such sensors for determining actual beam delivery information are further described with reference to FIG. 6.

FIG. 6 illustrates one embodiment of a process for use with systems and software for calculating an accumulated radiation dose utilizing actual beam delivery information consistent with certain aspects of the present disclosure. As further discussed herein, another improvement over current radiotherapy technology is that, rather than assuming that a planned radiation dose was delivered, the disclosed systems and processes utilize information about what the radiotherapy system actually delivered. By calculating the actual radiation dose delivered (e.g., on a moment-by-moment basis) the system can further calculate the actual accumulated actual dose to tissues during radiotherapy. As described further below, this facilitates other technical advances including improved radiation treatment plan reoptimization.

The process flow chart of FIG. 6 depicts one exemplary embodiment where, at 610, the system can deliver radiotherapy to a patient from a radiotherapy device. At 620, the system can acquire images of the patient from a magnetic resonance imaging system during the radiotherapy. At 630, the system can acquire actual beam delivery information during the radiotherapy, the actual beam delivery information including actual beam measurements including one or more of: measured monitor units, measured MLC leaf positions, measured gantry positions, measured couch positions and measured fluence profiles. At 640, the system can calculate the dose to tissues during the radiotherapy based on the acquired images and the acquired actual beam delivery information. At 650, the system can accumulate the dose to tissues during the radiotherapy.

With reference to operation 620, examples of acquired images can include single-planar, multi-planar (e.g., multiple parallel planes or non-parallel planes as described herein), volumetric (e.g., imaging sufficient to generate 3D patient volumes over time such as four volumes per second, eight volumes per second, etc.). As used herein, the term "acquired images" excludes modalities that may rely on features such as fiducials, skin surface tracking, etc., where treatment or planning relies on inferences regarding a patient's internal anatomy.

With reference to operation 630, rather than relying on planned radiation delivery characteristics, (e.g., planned monitor units, planned MLC leaf positions, etc.) the system can access or determine actual beam delivery information. For example, measured monitor units can be obtained from the beam output sensor 510, which can include radiation detectors such as monitor/ion chambers, diodes, pick-up coils, etc., that measure the actual output of the radiotherapy device. Similarly, rather than relying on planned MLC leaf positions, a determination of actual MLC leaf positions can be obtained, for example, by beam a shape sensor 522 that can view and analyze light from an interposed scintillator and camera system, by obtaining MLC leaf position encoder data, etc. Measured gantry positions can be determined with gantry sensors 532 that can include gantry angle position encoder data, exit radiation analysis (e.g., with an exit radiation detector that does not rotate with the gantry and therefore can discern changes in the incident angle of radiation), etc. Measured fluence profiles can be obtained with an exit radiation detector 542 such as an EPID or scintillator. Measured couch positions can be obtained from couch sensors 552 that may provide couch position encoder data.

With reference to operation 640, the system can obtain and provide any of the actual beam delivery information to a dose calculator for calculation of the actual dose delivered during radiotherapy. As used herein, the term "dose calculator" refers to a software program or module that is programmed to calculate a radiation dose to the patient from the beam delivery information and from information regarding the patient's anatomy. Examples of radiation dose output by the dose calculator can include 2D and/or 3D mappings of dose to the patient and can optionally be acquired over time to describe dose accumulation.

Figure 7:
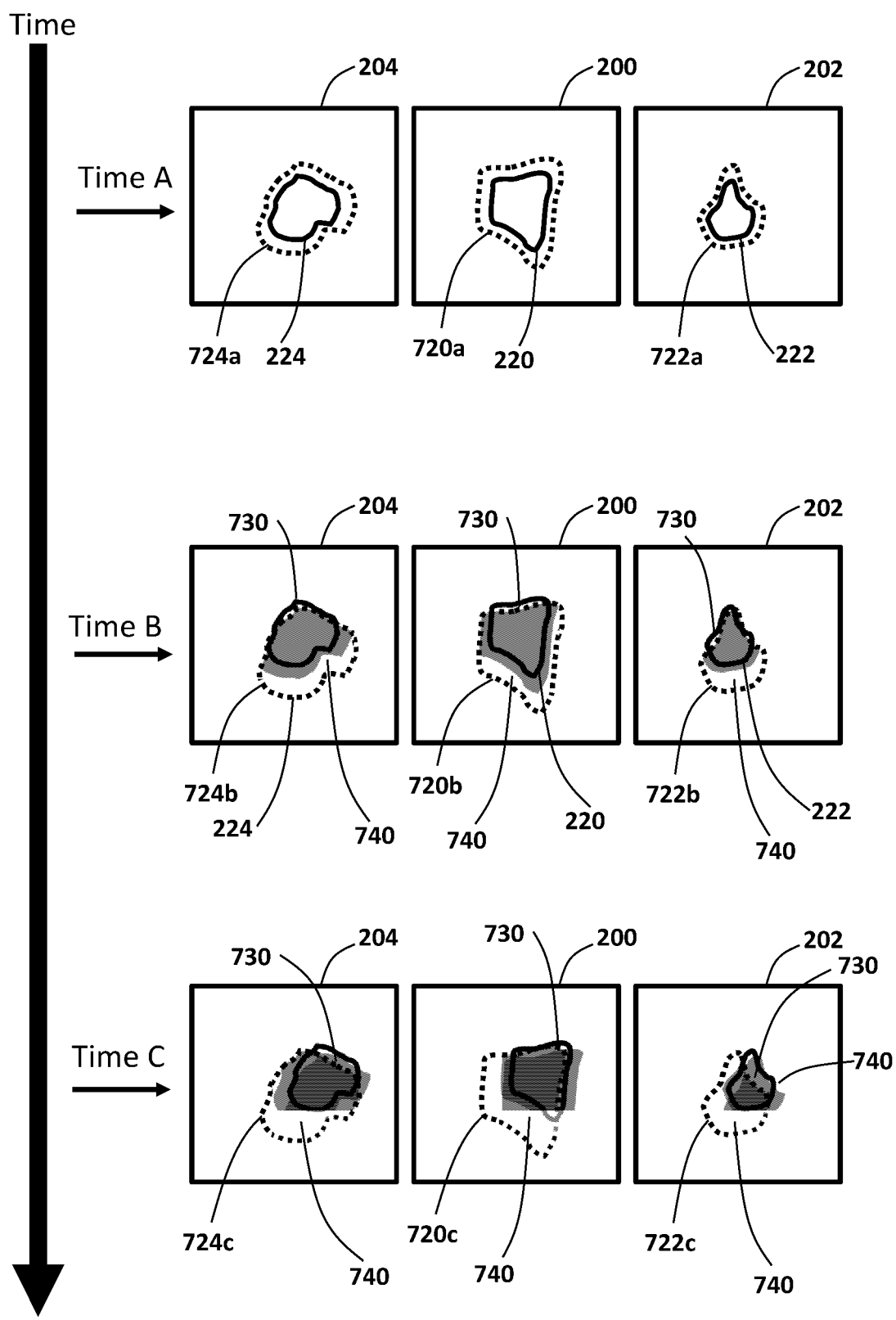
FIG. 7 provides a simplified illustration of the determination and display of accumulated radiation dose to patient tissues consistent with certain aspects of the present disclosure.

FIG. 7 provides an exemplary illustration of the determination and display of accumulated radiation dose to patient tissues consistent with certain aspects of the present disclosure. Because radiation may not always be delivered exactly to the target tissue, determining the actual accumulated dose can improve the ability of the system to meet the treatment prescription, which can be defined in terms of a desired dose to a target and permissible doses to other tissues/organs. Before describing how embodiments of the present disclosure perform reoptimization of radiation treatment plans based on the actual dose delivered to the patient, FIG. 7 depicts a system for determining and displaying the actual accumulated radiation dose.

FIG. 7 depicts the accumulation of radiation dose in three planes (200, 202, 204) showing projections of a target (220, 222, 224) similar to those described with reference to FIG. 2. Surrounding the target are corresponding regions of radiation dose deposition that can be made to conformally cover the target and also a slight margin around the target. FIG. 7 depicts this accumulation at three different times (time A, time B and time C). The amount of accumulated radiation is represented by intensity of the shaded regions. At time A, in the top panels, radiation is delivered in regions (720a, 722a, 724a) shown bounded by the dashed lines. At time B, in the middle panels, the patient shifts upward. Radiation is again delivered to the same location under the assumption that the target was static. Due to radiation being delivered to different locations of patient tissue (i.e., below where the target (220, 222, 224) presently is), there can be areas of underdose 730 to the target and overdose 740 to nearby tissue. At time C, in the lower panels, this process continues as the patient shifts to the right and radiation is delivered at yet a different location. While the accumulated radiation depicted in FIG. 7 is not ideal, the present disclosure's utilization of actual beam delivery information to calculate accumulated dose in conjunction with real-time imaging enables the system to measure such. With this information, disclosed embodiments can allow for the reoptimization or replanning of treatment to account for the known actual accumulated radiation dose. Such improved measurement and/or reoptimization procedures can therefore reduce or eliminate deviations from the radiation prescription.

The disclosed systems can display (e.g., on a display device such as a computer monitor) the accumulated dose to tissues during radiotherapy. The displaying can occur during radiotherapy and/or after radiotherapy. In some embodiments, display of the accumulated dose can be superimposed onto the images acquired during radiotherapy. In this way, patient anatomical structures that appear in MRI images can be associated with the delivered dose. To facilitate the determination and display of accumulated dose during radiotherapy, some embodiments can include displaying the accumulated dose on a most recent set of MRI images. In this way, the dose calculator and/or clinicians can be provided with the most up-to-date dose map for the patient's tissues. Dose can be displayed in a number of formats, for example, displaying the accumulated dose in multiple imaging planes, for example in three orthogonal planes, as depicted in FIG. 7.

In some implementations, determination of accumulated dose can be incorporated with gating operations (e.g., to prevent excessive unwanted delivery of radiation outside of permissible dose margins). In yet other implementations, additionally or alternatively, the system can reoptimize the radiation treatment plan to take into account the actual accumulated dose at a particular stage of radiotherapy. One exemplary process that can incorporate both gating and reoptimization can include, for example, the system contouring an anatomical structure of the patient, such as depicted in FIG. 7 and described elsewhere herein. The system can then, for example via a dose calculator, then determine accumulated dose to contoured anatomical structures. In some embodiments, the system can provide a notification or alarm if the accumulated dose to the contoured anatomical structure exceeds a specified limit. Such specified limits can be provided by the radiation prescription that can be set prior to the delivery of radiation. Similarly, the system can be configured to stop the delivery of radiotherapy if/when the accumulated dose to the contoured anatomical structure exceeds the specified limit. For example, if a particular organ at risk during a prostate treatment (e.g., the rectum) has accumulated more than an exemplary prescription's 10.8 Gy limit, radiotherapy may be terminated rather than continuing treatment as would be done in conventional systems not having the capabilities described herein.

Furthermore, the disclosed systems can determine a reoptimized treatment plan if accumulated dose to a contoured anatomical structure exceeds a specified limit. In some beneficial embodiments, determining the reoptimized treatment plan takes into account the accumulated dose and accounts for any under dosage or over dosage. For example, referring to FIG. 7, when a region of underdose 730 or overdose 740 (relative to what it should be in the current treatment plan) is identified, the treatment plan can adjust the subsequent radiation delivery parameters (e.g., MLC positions, gantry angle, etc.) such that the reoptimized treatment plan meets the prescription. While the reoptimized plan may be immediately implemented, in some implementations gating (e.g., interruption of radiotherapy) can continue until the system receives clinician approval of the reoptimized treatment plan.

In an embodiment with sufficient processing power, cessation of radiation delivery can be for a very short period of time so that the system can continually reoptimize the radiation treatment plan as quickly as patient imaging (or other limiting processes) can occur.

Figure 8:
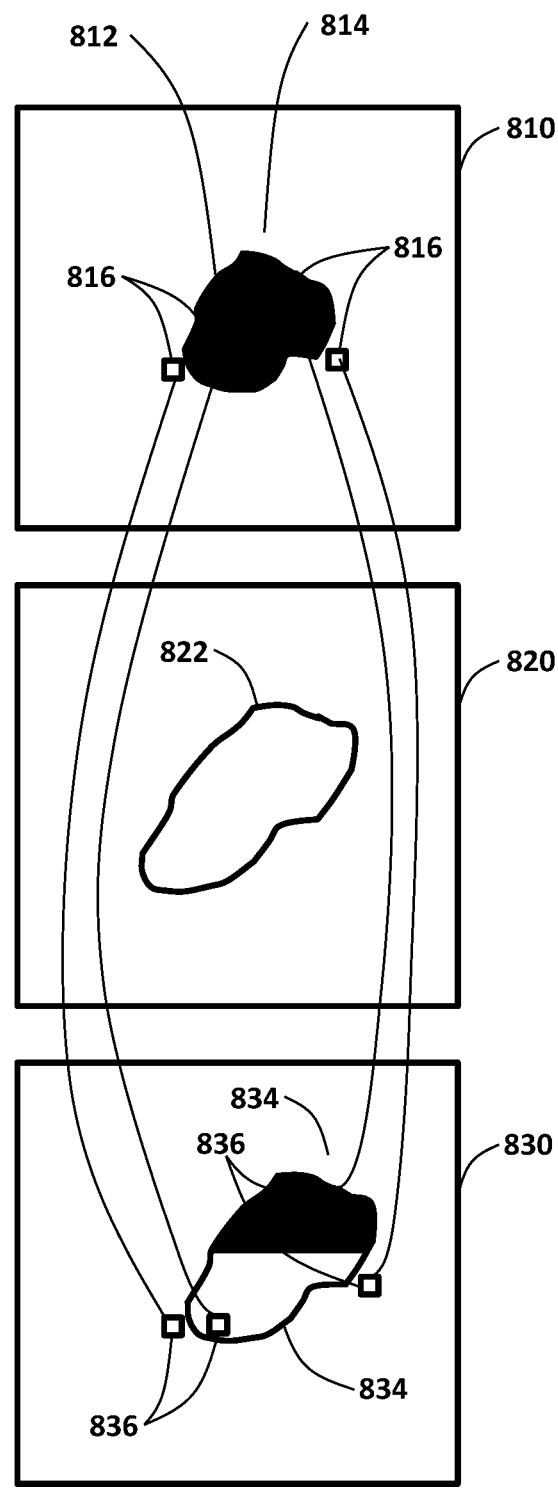
FIG. 8 provides a simplified illustration of the use of deformable image registration (DIR) to track accumulated dose during radiotherapy consistent with certain aspects of the present disclosure.

FIG. 8 illustrates an exemplary system utilizing deformable image registration to track accumulated dose during radiotherapy consistent with certain aspects of the present disclosure. In some embodiments, techniques involving deformable image registration can further improve the utilization of accumulated dose by accurately tracking dose that has been deposited even when tissue deforms during radiotherapy. As depicted in FIG. 8, the system calculating and/or accumulating dose to tissues can utilize deformable image registration and the most recent set of MRI images. As the present disclosure contemplates numerous embodiments relating to real-time imaging and dose calculation, the term "most recent" can refer to MRI images generated very close to the current time during radiotherapy such that they are substantially representative of the current state of the patient. In this way, while "most recent" can include literally the latest MRI images, it is contemplated that such also can include MRI images that may have been acquired up to 0.25 s previously.

In FIG. 8, the top panel 810 illustrates an exemplary target 812 and dose distribution 814 generally conforming to the target. A few example pixels (or voxels) are depicted that represent locations 816 that have received a given dose. The middle panel 820 illustrates deformed target 822, which represents a stretching of target 812. This panel can also be considered an example of a most recent MRI image. By utilizing deformable image registration, the system can generate a mapping between locations in the MRI image showing the deformed target and the prior MRI image. The bottom panel 830 depicts the system applying the mapping to the dose distribution 814 to deformably register the dose distribution onto the subsequent (or most recent) MRI image to form an updated dose distribution 834. The updated locations 836 of the locations 816 are also depicted. By performing this process on an ongoing basis during radiation delivery, the system can accurately accumulate dose in the most recent set of MRI images.

In some embodiments, the system can also perform such dose calculation/accumulation based on the inclusion of assigned relative electron densities. As part of radiation therapy planning, different materials within the patient (e.g., water, tissue, bone, etc.) can have different electron densities which affect their ability to receive radiation dose. The system, optionally with the input provided manually by a clinician, can assign such relative electron densities to identified anatomical structures. Similarly, to the extent that such structures deform as previously discussed, the mapping can also be applied to the relative electron densities to facilitate accurate dose calculations for those deformed structures.

Similar to other embodiments disclosed herein, the system can cause the display of accumulated dose in the images acquired during radiotherapy by using deformable image registration between the most recent set of MRI images and the images acquired during radiotherapy.

In some embodiments, calculating the dose to tissues further utilizes independent measurements of the magnetic resonance imaging system (e.g., measuring control system/gradient pulses/etc. rather than utilizing the MRI's time stamps) and independent measurements of the radiotherapy device (e.g., ion chamber readout) in order to synchronize the acquired images and acquired actual beam information.

The concepts described above with regard to dose calculation and accumulation can be integrated with the later-described prognostic motion model/prognostic motion adapted radiation treatment plan embodiments. One example of such an integration is provided in the discussion below relating to FIG. 13.

One prior limitation in the delivery of MRI-guided radiotherapy has been that, even if a patient is imaged in real-time, therapy devices have had a limited ability to adapt to patient motions and deliver therapy consistent with such motions. However, the present disclosure addresses these challenges at least partially through the utilization of prognostic motion models. With a prognostic motion model, expected movements of the patient are known to the MRgRT system and the planning and delivery of radiotherapy can be performed in a way to account for such motions, improve dose distributions, speed up therapy and account for latencies in the system between patient imaging and the delivery of radiation. A radiation treatment plan that utilizes such a prognostic motion model is referred to herein as a prognostic motion adapted radiation treatment plan.

FIG. 9 illustrates the generation of a prognostic motion model and a prognostic motion adapted radiation treatment plan consistent with certain aspects of the present disclosure. The prognostic motion model can include a model of expected patient movement during treatment. In some embodiments, an MRgRT system can be configured to perform operations including, at step 910, acquiring pretreatment images with a magnetic resonance imaging system, the pre-treatment images capturing movement of a patient. Then (at step 920), the system can generate a prognostic motion model based on at least the pre-treatment images. At step 930, the system can generate a prognostic motion adapted radiation treatment plan based at least on the prognostic motion model.

With reference to operation 910, pre-treatment images can include cine MRI (e.g., 2D or 3D MRI images of a patient over a time span), phase-binned MRI (e.g., MRI images taken not necessarily in sequence but grouped to effectively generate a representation of patient motion over a time span), etc. Ideally, these pretreatment images would permit the reconstruction of patient anatomy and movement at a high temporal resolution. However, the present disclosure contemplates that there may be gaps in the acquired pretreatment images. Accordingly, it is not essential that the pretreatment images are a continuous (or nearly continuous) representation of patient movement. Rather, they may be a sequence of images sufficient to enable the development and implementation of motion adapted radiation treatment plans as described herein. In particular embodiments, the pretreatment images can be acquired at exemplary rates of, for example, 2, 4, 8, 16, or 32 frames per second for 2D images and 1, 2, or 4 volumes per second for reconstruction of typical 3D patient volumes. In some embodiments, time-dependent 3D volume reconstruction can occur at the same rate as the acquisition of its composite 2D images. Operations 920 and 930 of FIG. 9 are described below with reference to FIG. 10.

In some embodiments, generating the prognostic motion model further includes excluding pre-treatment image(s) not representative of the expected patient movement during treatment. For example, if during acquisition of the pre-treatment images, the patient coughed, shifted or otherwise made motions that are atypical and not expected to be replicated during the actual treatment session, such images can be excluded from the model. In some embodiments, these images can be deleted by a clinician reviewing the pretreatment images at a display device. In other embodiments, these images can be deleted by the system by detecting excessive differences between images or groups of images. Such detection can occur by, for example, performing image analysis to identify anatomical structures, reference points, etc., and determining deviations from an expected location. For example, if the location of an anatomical structure varies over 2 cm during a typical breathing cycle, but some of the pre-treatment images depict the anatomical structure 5 cm from its expected (or average) location, such pre-treatment images can be excluded from the prognostic motion model.

In certain embodiments, the prognostic motion model can include multiple types of motion observed in the pretreatment images. For example, the multiple types of motion can include expected patient movement and irregular patient movement. These motions can be accounted for in planning and delivery, as described further below. Examples of some of the multiple types of motion that may observed and included within the model are regular motion due to breathing, motion due to deep breathing, motion due to GI system gas movement, motion due to bladder filling, chest-wall breathing, diaphragm breathing, motion due to swallowing, cardiac motion, patient movement (e.g., shifting, turning, etc.), motion due to talking, eye movement, voluntary muscle motion (e.g., scrunching or tensing/relaxing), etc.

While conventional radiation therapy plans assume a static patient anatomy, embodiments of the disclosed systems can generate a prognostic motion adapted radiation treatment plan that takes into account the prognostic motion model's expected patient movement during treatment.

The expected patient movement during treatment can include movement of a target to be treated. When a prognostic motion adapted radiation treatment plan takes into account the expected movement of a target in determining where and when therapy will be delivered, it can provide more accurate dose delivery than a plan not adapted in this way. For example, a prognostic motion adapted radiation treatment plan can take into account movement of the target that is small enough to avoid beam gating in a conventional system but large enough to result in dose being delivered off-target. For example, while a conventional MRgRT system may have the capability to gate off radiation when the beam deviates significantly from the target, it can nevertheless allow a beam slightly off target to continue delivering radiation for a significant period of time. In this way, a conventional system can deliver an excessive dose outside of the target. In contrast, a prognostic motion adapted radiation treatment plan can better account for the location and shape of the target due to its prognostic motion model and avoid such off-target dosing.

A prognostic motion adapted radiation treatment plan can also take into account an expected patient movement during treatment that is a deformation of a target or an organ of interest, because radiation therapy targets and nearby organs at risk not only move during therapy, they also deform.

Figure 10:
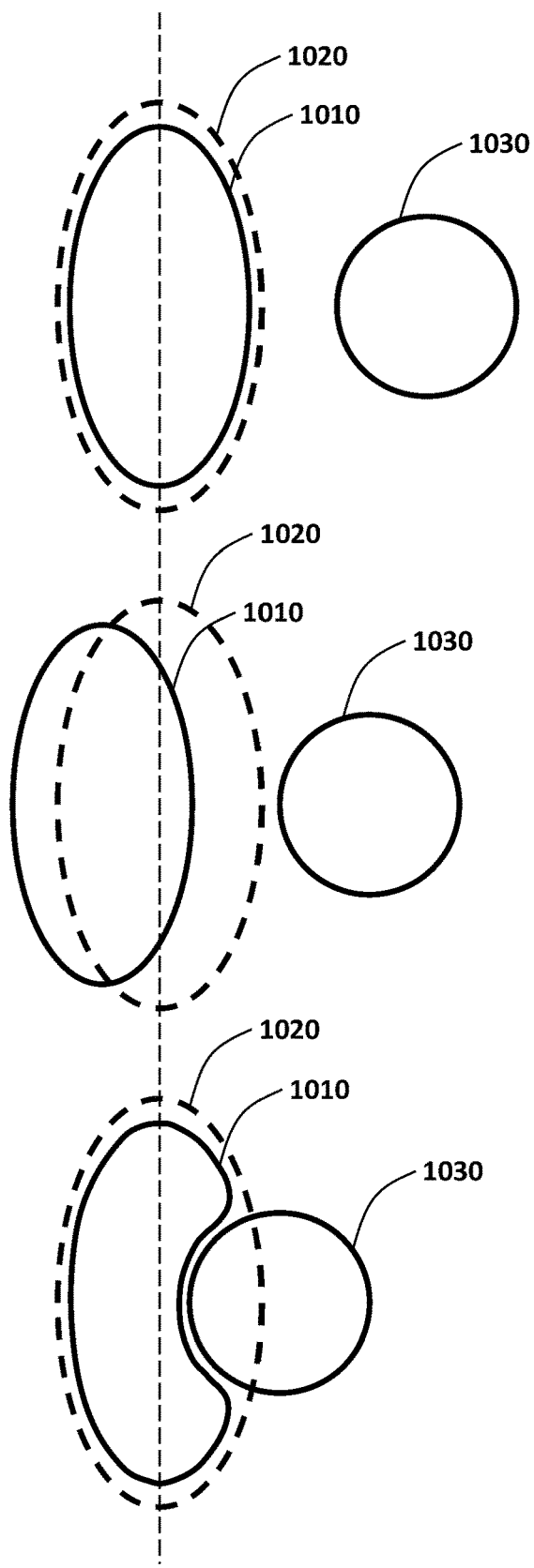
FIG. 10 is a simplified illustration detailing one exemplary benefit that can be achieved using a prognostic motion adapted radiation treatment plan accounting for tissue deformation consistent with certain aspects of the present disclosure.

FIG. 10 illustrates, in a simplified manner, one way in which such a prognostic motion adapted radiation treatment plan can account for tissue deformation better than conventional radiotherapy treatments. At the top of the FIG. 10, a target 1010 is surrounded by a spatial gating limit 1020, and to the right is an organ of interest 1030 (e.g., an organ that should not receive radiation, like a blood vessel).

Conventional radiation therapy plans, based on static imaging, will presume that target 1010 and organ of interest 1030 will maintain this same spatial relationship to one another (e.g., 5 mm apart). Such conventional systems may adequately handle movement demonstrated in the second row of FIG. 10—where the target and the organ of interest both move to the left and the target's deviation from the spatial gating limit 1020 causes the beam to gate off. However, a conventional system will not adequately handle the movement shown in the third row of FIG. 10—where movement and deformation both occur, the target does not exceed the spatial gating limit 1020, the beam consequently does not gate off, and the organ of interest 1030 is then exposed to radiation and damage. The beneficial technologies of the present disclosure, utilizing prognostic motion adapted radiation treatment plans would instead be aware that during a particular patient motion phase, the organ of interest would deform into the path of the beam and thus the plan would stop delivery during that motion phase, sparing the organ of interest from damaging radiation.

Similarly, some embodiments of a prognostic motion adapted radiation treatment plan can take into account a prognostic motion model's expected patient movement and also irregular patient movement during treatment. As an example of how the prognostic motion adapted radiation treatment plan can take into account irregular patient movement, the prognostic motion adapted radiation treatment plan can adjust or stop delivery when an irregular patient movement in the prognostic motion model is observed by the imaging system during treatment. As one example of adjusting radiation delivery, the patient motion model may include patient movements that are identified as irregular patient movement such as gas movement through a patient's gastrointestinal tract that causes movement of a target prostate. The prognostic motion adapted radiation treatment plan can then cause the delivery of radiation to stop when such an irregular patient movement is detected. In another embodiment, the prognostic motion adapted radiation treatment plan could cause the MRgRT system to deliver radiation in line with the irregular patient movement identified by the prognostic motion model. Such an implementation has the advantage of avoiding interruptions in the delivery of radiation that could extend a patient's treatment time.

The present disclosure contemplates that the prognostic motion adapted radiation treatment plan can also take into account a latency between patient movement observed with the magnetic resonance imaging system and radiation beam delivery to the patient. There are delays, or latency, between the time when a patient moves and when the MRI image reconstruction takes place and when the delivery of radiation can be adjusted (e.g., beam on/off, MLC leaf positions adjusted, gantry rotated, etc.). None of these operations happen instantaneously and latency is understood herein to include any combination of hardware and/or software delays. By taking into account these delays, the prognostic motion adapted radiation treatment plan can aim the radiation beam where the target is expected to be based on the prognostic motion model and latency, rather than to a specific point in space where one hopes the target will be.

FIG. 11 illustrates one embodiment of a process for delivering radiotherapy according to a prognostic motion adapted radiation treatment plan consistent with certain aspects of the present disclosure. At 1110, the system can acquire treatment images of a patient from a magnetic resonance imaging system, the treatment images capturing movement of a patient. At 1120, the system can deliver radiotherapy to the patient from a radiotherapy device according to a prognostic motion adapted radiation treatment plan based at least on a prognostic motion model.

In some embodiments, the system can be configured to identify a current patient movement from the treatment images. Various embodiments of the disclosed systems can identify a current patient movement (for example, through any of the processes described below in the discussion relating to FIG. 12). The system can then be configured to begin delivery of radiotherapy when the current patient movement matches an expected patient movement included in the prognostic motion model. As used herein, the term "matches" does not necessarily require an exact match between current patient movement and expected patient movement (though in some embodiments such may be utilized). Instead, in various embodiments, there may be permissible deviation between the movement determined from treatment images and the expected movement of the patient. The system can be configured to accept variations in movement such as 1%, 2%, 5% or 10% in any particular direction. As another example, the system can be configured to begin delivery of radiotherapy when overlap between the actual target volume location and the expected target volume location over time is small such as 1%, 2%, 5%, or 10% overlap. Furthermore, the beginning of radiotherapy can further account for a latency between the current patient movement observed with the magnetic resonance imaging system and radiation beam delivery to the patient.

Figure 12:
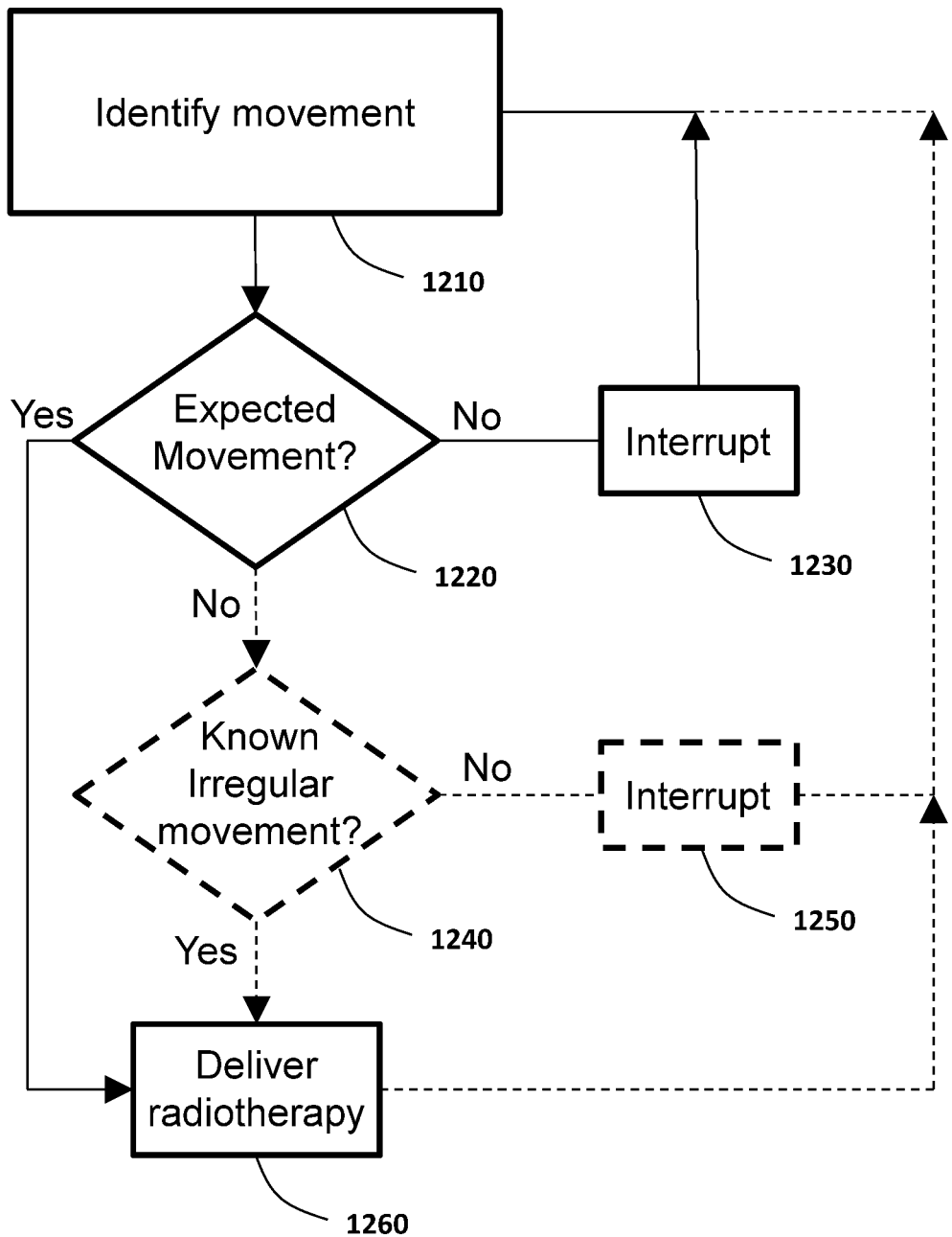
FIG. 12 illustrates exemplary processes for delivering radiotherapy based on a prognostic motion adapted treatment plan model consistent with certain aspects of the present disclosure.

FIG. 12 illustrates one embodiment of a process for delivering radiotherapy when patient movement follows a prognostic motion model. In the exemplary process, at 1210, the system can identify movement of the patient from the acquired treatment images. The present disclosure contemplates numerous algorithms for identifying whether movement of the patient in the acquired treatment images is expected based on the prognostic motion model.

In some embodiments, the system can directly compare images of the patient with those in the prognostic motion model and determine, based on a similarity calculation between the images, whether a given image conforms to an expected patient motion. Such similarity calculations can include pixel comparisons, determining a correlation coefficient, etc.

In other embodiments, the system can determine whether the movement of the patient conforms to the prognostic motion adapted radiation treatment plan by utilizing a tissue probability distribution based on the prognostic motion model. An exemplary process can include, determining a tissue probability distribution utilizing the prognostic motion model, the tissue probability distribution quantifying probable locations of patient tissues during expected patient movement. The system can then compare a tissue distribution of the patient from the treatment images to the tissue probability distribution. Radiotherapy can be delivered when the comparison indicates the tissue distribution is sufficiently probable to represent the expected patient movement.

In some embodiments, the system can determine whether the trajectories of tissue in the patient conform to the prognostic motion adapted radiation treatment plan utilizing expected patient tissue trajectories based on the prognostic motion model. An exemplary process can include, determining an expected patient tissue trajectory utilizing the prognostic motion model, the expected patient tissue trajectory quantifying expected trajectories of patient tissues during expected patient movement. The system can then compare patient tissue trajectory of the patient from the treatment images to the expected patient tissue trajectory. Radiotherapy can be delivered when the comparison indicates the patient tissue trajectory is sufficiently similar to expected patient tissue trajectory.

In yet other embodiments, the system can determine whether the differential movements of tissue in the patient conform to the prognostic motion adapted radiation treatment plan utilizing expected patient tissue differential movements based on the prognostic motion model. An exemplary process can include, determining an expected patient tissue differential movement utilizing the prognostic motion model, the expected patient tissue differential movement quantifying expected differential movement of patient tissues during expected patient movement. The system can then compare patient tissue differential movement of the patient from the treatment images to the expected patient tissue differential movement. Radiotherapy can be delivered when the comparison indicates the patient tissue differential movement is sufficiently similar to expected patient tissue differential movement.

At step 1220 of FIG. 12, the system can determine whether the patient movement is expected movement. For example, identified movements can be compared to the types of movement (i.e., expected movement) associated with the prognostic motion adapted radiation treatment plan. If the identified movement matches the expected movement, then therapy can be delivered according to the portion of the plan created for expected movement. If the identified movement does not match the expected movement, certain embodiments can interrupt therapy at step 1230 (e.g., gating the beam off). In another embodiment, if the identified movement is not the expected movement, the system can check at step 1240 to determine whether the identified movement is a known irregular movement. In some embodiments, the identification of a known irregular movement can result in the interruption/gating of therapy at step 1250. In other embodiments, when a known irregular movement is identified, the prognostic motion adapted treatment plan can deliver therapy in line with that known irregular movement at operation 1260.

In response to an interruption or gating of therapy, the system can continue to monitor and identify patient movement and may resume the delivery of radiotherapy according to the prognostic motion adapted radiation treatment plan at a phase when the movement of the patient returns to the expected patient movement.

As used herein, the term "at a phase" means when the observed patient motion/location of anatomical structures returns to a state similar to that prior to treatment being interrupted. For example, if the prognostic motion model included a patient breathing normally and the patient coughed, causing the system to gate, resumption of radiotherapy may not begin until further imaging and analysis determined that the patient had resumed normal breathing. In an embodiment, this can further include waiting until a particular state of motion is identified. For example, if the radiotherapy gated at a full exhale, then the system may resume the delivery of radiotherapy only when another full exhale is identified current patient motion. In some embodiments, this can include requiring the patient movement to match expected movements for a particular period of time, for example, one second, 30 seconds, one minute, etc., to ensure that unacceptable motions ceased.

In cases where patient motion during treatment is not matching up well with the prognostic motion model, the system can be configured to generate a second prognostic motion model utilizing the acquired treatment images. The system can then generate a second prognostic motion adapted radiation treatment plan based at least on the second prognostic motion model. In some embodiments, the second prognostic motion model may be an entirely new model, but in other embodiments it may be a revised model. The system can generate such a revised second prognostic motion model based on the inclusion/editing/replacement images making up the prognostic motion, such as expanding the image set to include images of deeper breathing, etc.

After creating the second prognostic motion adapted radiation treatment plan, the system can resume the delivery of radiotherapy utilizing the second prognostic motion adapted radiation treatment plan. In one implementation, the second prognostic motion adapted radiation treatment plan can be presented (e.g., via a display device) to a clinician for approval prior to the resumption of therapy. In another embodiment, the system can continuously update the prognostic motion model and the prognostic motion adapted radiation treatment plan in order to best match the current motion of the patient on the treatment table.

Many of the technical improvements provided by the present disclosure can be combined to provide even greater accuracy and efficiency in delivering radiotherapy. For example, the present disclosure (e.g., with reference to FIG. 6) describes improved dose calculation and accumulation techniques based on the acquisition of actual beam delivery information during radiotherapy. Such features can be incorporated into the generation and use of a prognostic motion adapted radiation treatment plan as described herein. FIG. 13 depicts an exemplary embodiment of a process combining such features.

At 1310, a system can be configured to acquire actual beam delivery information during radiotherapy, the actual beam delivery information comprising actual beam measurements including one or more of: measured monitor units, measured MLC leaf positions, measured gantry positions, measured couch positions and measured fluence profiles.

At 1320, the system can calculate dose to tissues during the radiotherapy based on the acquired images and the acquired actual beam delivery information.

At 1330, the system can accumulate dose to tissues during the radiotherapy. At 1340, the system can generate a second prognostic motion adapted radiation treatment plan if the accumulated dose to an anatomical structure exceeds a specified limit. Similar to the operation described above, the second prognostic motion adapted radiation treatment plan can be a revised/edited plan or may be an entirely new plan utilizing a new prognostic model. Also, the system can generate the second prognostic motion adapted radiation treatment plan taking into account the accumulated dose and accounting for any under dosage or over dosage. For example, the number, orientation, and time, of radiation beams to be delivered can be adjusted to best meet the prescription. In addition, the system can generate a second prognostic motion adapted radiation treatment plan that takes into account a second prognostic motion model utilizing the acquired treatment images, similar to the technique described above.

At 1350, the system can continue the delivery of radiotherapy utilizing the second prognostic motion adapted radiation treatment plan. In one embodiment, the new radiation treatment plan can be displayed to a clinician for reviewing, editing, and approval. However, the system can also be configured to refer to a set of tolerances (e.g., dose volume histogram or total dose constraints) and, if the system is able to generate a reoptimized treatment plan that is still within the tolerances and dose constraints, the system may then implement the new reoptimized treatment plan and continue to deliver radiotherapy with little or no interruption resulting from the reoptimization. Accordingly, the radiation treatment plan can be reoptimized for optimal target coverage and organ sparing, and maximum efficiency.

In the following, further features, characteristics, and exemplary technical solutions of the present disclosure will be described in terms of items that may be optionally claimed in any combination:

Item 1: A non-transitory, machine-readable medium storing instructions which, when executed by at least one programmable processor, cause the at least one programmable processor to perform operations comprising: acquiring real-time images of a patient from a magnetic resonance imaging system in at least two non-parallel planes; contouring an anatomical structure of the patient in the at least two non-parallel planes; setting spatial limits for movement of the anatomical structure in the at least two non-parallel planes; controlling a radiotherapy device to deliver a radiotherapy beam to the patient; and gating off the radiotherapy beam when the anatomical structure exceeds a spatial limit in either of the at least two non-parallel planes.

Item 2: The machine-readable medium of Item 1, wherein the at least two non-parallel planes are three orthogonal planes.

Item 3: The machine-readable medium of any one of the preceding Items, wherein the at least two non-parallel planes are orthogonal.

Item 4: The machine-readable medium of any one of the preceding Items, wherein the at least two non-parallel planes are oblique.

Item 5: The machine-readable medium of any one of the preceding Items, wherein the acquiring of the real-time images from the magnetic resonance imaging system in at least two non-parallel planes is performed by energizing and controlling one or more subsystems of a gradient coil system of the magnetic resonance imaging system.

Item 6: The machine-readable medium of any one of the preceding Items, wherein the acquiring of the real-time images from the magnetic resonance imaging system in at the least two non-parallel planes includes T1 and T2 weighted volumetric scans at an SRS isocenter.

Item 7: The machine-readable medium of any one of the preceding Items, wherein the contouring of the anatomical structure of the patient is performed via machine autocontouring.

Item 8: The machine-readable medium of any one of the preceding Items, wherein the contouring of the anatomical structure of the patient is performed via a machine receiving manual user input.

Item 9: The machine-readable medium of any one of the preceding Items, wherein the radiotherapy device is further controlled to deliver stereotactic radiosurgery (SRS) to the patient.

Item 10: The machine-readable medium of any one of the preceding Items, wherein the magnetic resonance imaging system operates at a field strength of less than 1.0 Tesla.

Item 11: The machine-readable medium of any one of the preceding Items, wherein the spatial limits are set within 0.5 mm of the boundaries of the anatomical structure in the at least two non-parallel planes.

Item 12: A non-transitory, machine-readable medium storing instructions which, when executed by at least one programmable processor, cause the at least one programmable processor to perform operations comprising: delivering radiotherapy to a patient from a radiotherapy device; acquiring images of the patient from a magnetic resonance imaging system during the radiotherapy; acquiring actual beam delivery information during the radiotherapy, the actual beam delivery information comprising actual beam measurements including one or more of: measured monitor units, measured MLC leaf positions, measured gantry positions, measured couch positions and measured fluence profiles; calculating dose to tissues during the radiotherapy based on the acquired images and the acquired actual beam delivery information; and accumulating dose to tissues during the radiotherapy, and optionally including any of the preceding Items.

Item 13: The machine-readable medium of any one of the preceding Items, the operations further comprising: displaying accumulated dose to tissues during radiotherapy.

Item 14: The machine-readable medium of any one of the preceding Items, the operations further comprising displaying the accumulated dose on the images acquired during radiotherapy.

Item 15: The machine-readable medium of any one of the preceding Items, the operations further comprising displaying the accumulated dose on a most recent set of MRI images.

Item 16: The machine-readable medium of any one of the preceding Items, the operations further comprising displaying the accumulated dose in a plurality of imaging planes.

Item 17: The machine-readable medium of any one of the preceding Items, the operations further comprising displaying the accumulated dose in three orthogonal planes.

Item 18: The machine-readable medium of any one of the preceding Items, the operations further comprising: contouring an anatomical structure of the patient; determining accumulated dose to a contoured anatomical structure; providing a notification or alarm if the accumulated dose to the contoured anatomical structure exceeds a specified limit; stopping the delivery of radiotherapy if the accumulated dose to the contoured anatomical structure exceeds the specified limit; and determining a reoptimized treatment plan if the accumulated dose to the contoured anatomical structure exceeds the specified limit.

Item 19: The machine-readable medium of any one of the preceding Items, wherein determining the reoptimized treatment plan takes into account the accumulated dose and accounts for any under dosage or over dosage.

Item 20: The machine-readable medium of any one of the preceding Items, wherein calculating the dose to tissues further utilizes deformable image registration and the most recent set of MRI images including assigned relative electron densities.

Item 21: The machine-readable medium of any one of the preceding Items, wherein accumulating dose to tissues further utilizes deformable image registration and the most recent set of MRI images including assigned relative electron densities.

Item 22: The machine-readable medium of any one of the preceding Items, wherein dose is accumulated in the most recent set of MRI images.

Item 23: The machine-readable medium of any one of the preceding Items, the operations further comprising displaying accumulated dose in the images acquired during radiotherapy using deformable image registration between the most recent set of MRI images and the images acquired during radiotherapy.

Item 24: The machine-readable medium of any one of the preceding Items, wherein calculating the dose to tissues further utilizes independent measurements of the magnetic resonance imaging system and the radiotherapy device in order to synchronize the acquired images and acquired actual beam information.

Item 25: A non-transitory, machine-readable medium storing instructions which, when executed by at least one programmable processor, cause the at least one programmable processor to perform operations comprising: acquiring pre-treatment images with a magnetic resonance imaging system, the pre-treatment images capturing movement of a patient; generating a prognostic motion model based on at least the pre-treatment images; and generating a prognostic motion adapted radiation treatment plan based at least on the prognostic motion model, and optionally including any of the preceding Items.

Item 26: The machine-readable medium of any one of the preceding Items, wherein the pre-treatment images comprise cine MRI.

Item 27: The machine-readable medium of any one of the preceding Items, wherein the prognostic motion model comprises a model of expected patient movement during treatment.

Item 28: The machine-readable medium of any one of the preceding Items, wherein generating the prognostic motion model further comprises excluding pre-treatment image(s) not representative of the expected patient movement during treatment.

Item 29: The machine-readable medium of any one of the preceding Items, wherein generating the prognostic motion model further comprises including multiple types of motion observed in the pre-treatment images.

Item 30: The machine-readable medium of any one of the preceding Items, wherein the multiple types of motion include expected patient movement and irregular patient movement.

Item 31: The machine-readable medium of any one of the preceding Items, wherein the multiple types of motion include one or more of: regular motion due to breathing, motion due to deep breathing, motion due to GI system gas movement, motion due to bladder filling, motion due to patient movement, motion due to swallowing, chest-wall breathing, diaphragm breathing, talking, eye movement, cardiac motion, or voluntary muscle motion.

Item 32: The machine-readable medium of any one of the preceding Items, wherein the prognostic motion adapted radiation treatment plan takes into account the prognostic motion model's expected patient movement during treatment.

Item 33: The machine-readable medium of any one of the preceding Items, wherein the expected patient movement during treatment includes deformation of a target or an organ of interest.

Item 34: The machine-readable medium of any one of the preceding Items, wherein the expected patient movement during treatment includes movement of a target.

Item 35: The machine-readable medium of any one of the preceding Items, wherein the prognostic motion adapted radiation treatment plan takes into account movement of the target that is small enough to avoid beam gating but large enough to result in dose being delivered off-target.

Item 36: The machine-readable medium of any one of the preceding Items, wherein the prognostic motion adapted radiation treatment plan takes into account the prognostic motion model's expected patient movement and irregular patient movement during treatment.

Item 37: The machine-readable medium of any one of the preceding Items, wherein the prognostic motion adapted radiation treatment plan adjusts or stops delivery when the irregular patient movement of the prognostic motion model is observed during treatment.

Item 38: The machine-readable medium of any one of the preceding Items, wherein the prognostic motion adapted radiation treatment plan takes into account a latency between patient movement observed with the magnetic resonance imaging system and radiation beam delivery to the patient.

Item 39: The machine-readable medium of any one of the preceding Items, wherein the prognostic motion adapted radiation treatment plan aims the radiation beam where the target is expected to be based on the prognostic motion model and the latency rather than to a specific point in space.

Item 40: A non-transitory, machine-readable medium storing instructions which, when executed by at least one programmable processor, cause the at least one programmable processor to perform operations comprising: acquiring treatment images of a patient from a magnetic resonance imaging system, the treatment images capturing movement of a patient; and delivering radiotherapy to the patient from a radiotherapy device according to a prognostic motion adapted radiation treatment plan based at least on a prognostic motion model, and optionally including any of the preceding Items.

Item 41: The machine-readable medium of any one of the preceding Items, the operations further comprising: identifying a current patient movement from the treatment images; and beginning delivery of radiotherapy when the current patient movement matches an expected patient movement included in the prognostic motion model.

Item 42: The machine-readable medium of any one of the preceding Items, wherein the beginning of radiotherapy further accounts for a latency between the current patient movement observed with the magnetic resonance imaging system and radiation beam delivery to the patient.

Item 43: The machine-readable medium of any one of the preceding Items, wherein the delivered radiotherapy is aimed where a target is expected to be based on the prognostic motion model and a latency between patient movement observed with the magnetic resonance imaging system and radiation beam delivery to the patient, rather than to a specific point in space.

Item 44: The machine-readable medium of any one of the preceding Items, the operations further comprising: identifying the movement of the patient from the acquired treatment images.

Item 45: The machine-readable medium of any one of the preceding Items, the operations further comprising: delivering the radiotherapy to the patient when the movement of the patient matches an expected patient movement.

Item 46: The machine-readable medium of any one of the preceding Items, the operations further comprising: interrupting the delivery of radiotherapy when the movement of the patient does not match an expected patient movement.

Item 47: The machine-readable medium of any one of the preceding Items, the operations further comprising: interrupting the delivery of radiotherapy when the movement of the patient matches an irregular patient movement.

Item 48: The machine-readable medium of any one of the preceding Items, the operations further comprising: resuming the delivery of radiotherapy according to the prognostic motion adapted radiation treatment plan at a phase when the movement of the patient returns to the expected patient movement.

Item 49: The machine-readable medium of any one of the preceding Items, the operations further comprising: generating a second prognostic motion model utilizing the acquired treatment images; generating a second prognostic motion adapted radiation treatment plan based at least on the second prognostic motion model; and resuming the delivery of radiotherapy utilizing the second prognostic motion adapted radiation treatment plan.

Item 50: The machine-readable medium of any one of the preceding Items, the operations further comprising: acquiring actual beam delivery information during the radiotherapy, the actual beam delivery information comprising actual beam measurements including one or more of: measured monitor units, measured MLC leaf positions, measured gantry positions, measured couch positions and measured fluence profiles; calculating dose to tissues during the radiotherapy based on the acquired images and the acquired actual beam delivery information; accumulating dose to tissues during the radiotherapy; generating a second prognostic motion adapted radiation treatment plan if the accumulated dose to an anatomical structure exceeds a specified limit; and continuing the delivery of radiotherapy utilizing the second prognostic motion adapted radiation treatment plan.

Item 51: The machine-readable medium of any one of the preceding Items, wherein generating the second prognostic motion adapted radiation treatment plan takes into account the accumulated dose and accounts for any under dosage or over dosage.

Item 52: The machine-readable medium of any one of the preceding Items, wherein generating the second prognostic motion adapted radiation treatment plan takes into account a second prognostic motion model utilizing the acquired treatment images.

Item 53: A method comprising the operations of any of any one of the preceding Items.

Item 54: A system comprising: at least one programmable processor; and a non-transitory machine-readable medium storing instructions which, when executed by the at least one programmable processor, cause the at least one programmable processor to perform operations comprising those of any one of items 1-52.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A non-transitory, machine-readable medium storing instructions which, when executed by at least one programmable processor, cause the at least one programmable processor to perform operations comprising:
   acquiring real-time images of a patient from a magnetic resonance imaging system in at least two non-parallel planes;
   contouring an anatomical structure of the patient in the at least two non-parallel planes;
   setting spatial limits for movement of the anatomical structure in the at least two non-parallel planes;
   controlling a radiotherapy device to deliver a radiotherapy beam to the patient;
   gating off the radiotherapy beam when the anatomical structure exceeds a spatial limit for movement of the anatomical structure in either of the at least two non-parallel planes;
   acquiring actual beam delivery information during delivery of the radiotherapy beam, the actual beam delivery information comprising actual beam measurements including one or more of: measured monitor units, measured multileaf collimator leaf positions, measured gantry positions, measured couch positions and measured fluence profiles;
   calculating dose to tissues during the delivery of the radiotherapy beam based on the acquired real-time images and the acquired actual beam delivery information;
   accumulating dose to tissues during the delivery of the radiotherapy beam; and
   displaying the accumulated dose to tissues, during delivery of the radiotherapy beam, in three orthogonal planes.

2. The machine-readable medium of claim 1, wherein the at least two non-parallel planes are three orthogonal planes.

3. The machine-readable medium of claim 1, wherein the at least two non-parallel planes are orthogonal.

4. The machine-readable medium of claim 1, wherein the at least two non-parallel planes are oblique.

5. The machine-readable medium of claim 1, wherein the acquiring of the real-time images from the magnetic resonance imaging system in at least two non-parallel planes is performed by energizing and controlling one or more subsystems of a gradient coil system of the magnetic resonance imaging system.

6. The machine-readable medium of claim 1, wherein the acquiring of the real-time images from the magnetic resonance imaging system in at the least two non-parallel planes includes T1 and T2 weighted volumetric scans at a stereotactic radiosurgery (SRS) isocenter.

7. The machine-readable medium of claim 1, wherein the contouring of the anatomical structure of the patient is performed via machine autocontouring.

8. The machine-readable medium of claim 1, wherein the contouring of the anatomical structure of the patient is performed via a machine receiving manual user input.

9. The machine-readable medium of claim 1, wherein the radiotherapy device is further controlled to deliver stereotactic radiosurgery (SRS) to the patient.

10. The machine-readable medium of claim 1, wherein the magnetic resonance imaging system operates at a field strength of less than 1.0 Tesla.

11. The machine-readable medium of claim 1, wherein the spatial limits are set within 0.5 mm of the boundaries of the anatomical structure in the at least two non-parallel planes.

12. The machine-readable medium of claim 1, the operations further comprising:
   determining accumulated dose to a contoured anatomical structure;
   providing a notification or alarm if the accumulated dose to the contoured anatomical structure exceeds a specified limit;
   stopping the delivery of the radiotherapy beam if the accumulated dose to the contoured anatomical structure exceeds the specified limit; and
   determining a reoptimized treatment plan if the accumulated dose to the contoured anatomical structure exceeds the specified limit.

13. The machine-readable medium of claim 12, wherein determining the reoptimized treatment plan takes into account the accumulated dose and accounts for any under dosage or over dosage.

14. A non-transitory, machine-readable medium storing instructions which, when executed by at least one programmable processor, cause the at least one programmable processor to perform operations comprising:
   acquiring real-time images of a patient from a magnetic resonance imaging system in at least two non-parallel planes;
   contouring an anatomical structure of the patient in the at least two non-parallel planes;
   setting spatial limits for movement of the anatomical structure in the at least two non-parallel planes;
   controlling a radiotherapy device to deliver a radiotherapy beam to the patient;
   gating off the radiotherapy beam when the anatomical structure exceeds a spatial limit for movement of the anatomical structure in either of the at least two non-parallel planes;
   acquiring actual beam delivery information during delivery of the radiotherapy beam, the actual beam delivery information comprising actual beam measurements including one or more of: measured monitor units, measured multileaf collimator leaf positions, measured gantry positions, measured couch positions and measured fluence profiles;
   calculating dose to tissues during the delivery of the radiotherapy beam based on the acquired real-time images and the acquired actual beam delivery information; wherein calculating the dose to tissues further utilizes deformable image registration and the real-time images including assigned relative electron densities; and
   accumulating dose to tissues during the delivery of the radiotherapy beam.

15. A non-transitory, machine-readable medium storing instructions which, when executed by at least one programmable processor, cause the at least one programmable processor to perform operations comprising:
   acquiring real-time images of a patient from a magnetic resonance imaging system in at least two non-parallel planes;
   contouring an anatomical structure of the patient in the at least two non-parallel planes;
   setting spatial limits for movement of the anatomical structure in the at least two non-parallel planes;
   controlling a radiotherapy device to deliver a radiotherapy beam to the patient;
   gating off the radiotherapy beam when the anatomical structure exceeds a spatial limit for movement of the anatomical structure in either of the at least two non-parallel planes;
   acquiring actual beam delivery information during delivery of the radiotherapy beam, the actual beam delivery information comprising actual beam measurements including one or more of: measured monitor units, measured multileaf collimator leaf positions, measured gantry positions, measured couch positions and measured fluence profiles;
   calculating dose to tissues during the delivery of the radiotherapy beam based on the acquired real-time images and the acquired actual beam delivery information; and
   accumulating dose to tissues during the delivery of the radiotherapy beam; wherein accumulating dose to tissues further utilizes deformable image registration and the the real-time images including assigned relative electron densities.

16. The machine-readable medium of claim 15, wherein the dose is accumulated in the real-time images.

17. The machine-readable medium of claim 16, the operations further comprising displaying the accumulated dose in the real-time images acquired during delivery of the radiotherapy beam using deformable image registration between the the real-time images and the real-time images acquired during delivery of the radiotherapy beam.

18. The machine-readable medium of claim 17, wherein calculating the dose to tissues further utilizes independent measurements of the magnetic resonance imaging system and the radiotherapy device in order to synchronize the acquired real-time images and acquired actual beam information.

19. The machine-readable medium of claim 15, the operations further comprising: displaying the accumulated dose to tissues during delivery of the radiotherapy beam.

20. The machine-readable medium of claim 19, the operations further comprising displaying the accumulated dose on the real-time images acquired during delivery of the radiotherapy beam.

21. The machine-readable medium of claim 19, the operations further comprising displaying the accumulated dose on the real-time images.

22. The machine-readable medium of claim 19, the operations further comprising displaying the accumulated dose in a plurality of imaging planes.

23. The machine-readable medium of claim 22, the operations further comprising displaying the accumulated dose in three orthogonal planes.

* * * * *